(12) United States Patent
Stevens et al.

(10) Patent No.: US 9,975,925 B2
(45) Date of Patent: May 22, 2018

(54) INFLUENZA ANTIGENS AND ANTIBODIES

(71) Applicants: GLAXOSMITHKLINE BIOLOGICALS S.A., Rixensart (BE); THE UNITED STATES OF AMERICA, AS REPRESENTED BY THE SECRETARY OF THE DEPARTMENT OF HEALTH AND HUMAN SERVICES, Washington, DC (US)

(72) Inventors: James Stevens, Atlanta, GA (US); Ruben Donis, Atlanta, GA (US); David Shore, Atlanta, GA (US); Hongquan Wan, Atlanta, GA (US); Ventzislav Bojidarov Vassilev, Rixensart (BE)

(73) Assignees: GLAXOSMITHKLINE BIOLOGICALS S.A., Rixensart (BE); THE UNITED STATES OF AMERICA, REPRESENTED BY THE SECRETARY, DEPT. HEALTH & HUMAN SERVICES, Washington, DC (US)

( * ) Notice: Subject to any disclaimer, the term of this patent is extended or adjusted under 35 U.S.C. 154(b) by 0 days. days.

(21) Appl. No.: 14/914,431

(22) PCT Filed: Aug. 26, 2014

(86) PCT No.: PCT/EP2014/068108
§ 371 (c)(1),
(2) Date: Feb. 25, 2016

(87) PCT Pub. No.: WO2015/028478
PCT Pub. Date: Mar. 5, 2015

(65) Prior Publication Data
US 2016/0207963 A1    Jul. 21, 2016

Related U.S. Application Data

(60) Provisional application No. 61/870,862, filed on Aug. 28, 2013.

(51) Int. Cl.
*A61K 39/145* (2006.01)
*A61K 39/12* (2006.01)
*C07K 14/005* (2006.01)
*C07K 16/10* (2006.01)
*A61K 39/00* (2006.01)

(52) U.S. Cl.
CPC ........ *C07K 14/005* (2013.01); *C07K 16/1018* (2013.01); *A61K 39/00* (2013.01); *A61K 2039/505* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/76* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2007/0042001 A1* | 2/2007 | Weeks-Levy | A61K 39/145 424/209.1 |
| 2009/0169576 A1* | 7/2009 | Crea | A61K 39/145 424/186.1 |
| 2016/0207963 A1* | 7/2016 | Stevens | C07K 16/1018 |

FOREIGN PATENT DOCUMENTS

| | | |
|---|---|---|
| EP | 399843 | 11/1990 |
| WO | WO 1995/17210 | 1/1995 |
| WO | WO 2007/053446 A2 | 5/2007 |
| WO | WO 2010/006452 A1 | 1/2010 |
| WO | WO 2010/060430 A2 | 6/2010 |
| WO | WO 2011/044152 A1 | 4/2011 |
| WO | WO 2011/091376 A2 | 7/2011 |
| WO | WO 2012/082634 | 6/2012 |
| WO | WO 2015/028478 A1 | 3/2015 |

OTHER PUBLICATIONS

Yu et al. (Journal of Clinical Microbiology. 2008; 46 (3): 1067-1075).*
Bright et al. (Virology. 2003; 308: 270-278).*
Adel et al. (Research in Veterinary Science. 2017; 112: 132-140).*
Bragstad et al. (Virology Journal. 2008; 5 (40): 1-19).*
Chen et al. (PLoS ONE. Nov. 2012; 7 (11): e49224, pp. 1-11).*
Krammer (Expert Review of Vaccines. 2017; 16 (5): 503-513).*
Lin et al. (PLoS ONE. Jun. 2012; 7 (6): e39075: 1-8).*
Puthavathana et al. (Journal of General Virology. 2005; 86: 423-433).*
BE 2011400627 Search Report dated Jul. 10, 2015.
Sui, et al., "Structural and functional bases for broad-spectrum neutralization of avian and human influenza A viruses", Nature Structural and Molecular Biology, 16(3):265-273 (2009).
Kaverin, et al., "Structure of antigenic sites on the haemagglutinin molecule of H5 avian influenza virus and phenotypic variation of escape mutants", Journal of General Virology, 83:2497-2505 (2002).
Khurana, et al., "Antigenic fingerprinting of H5N1 Avian influenza using convalescent sera and monoclonal antibodies reveals potential vaccine and diagnostic targets", PLOS Medicine, 6(4):e1000049-e1000049 (2009).
Li, et al., "Characterisation and haemagglutinin gene epitope mapping of a variant strain of H5N1 subtype avian influenza virus", Veterinary Microbiology, 162(2-4):614-622 (2013).
Popova, et al., "Immunodominance of antigenic site B over site A of hemagglutinin of recent H3N2 influenza viruses", PLOS ONE, 7(7):e41895 (2012).

(Continued)

*Primary Examiner* — Shannon A. Foley
(74) *Attorney, Agent, or Firm* — Natalie A. Lissy

(57) ABSTRACT

Novel influenza antigens, novel immunogenic or vaccine compositions, as well as uses of and methods for producing said antigens and compositions, are described.

19 Claims, 11 Drawing Sheets

(56) References Cited

OTHER PUBLICATIONS

Yoshida, et al., "Cross-protective potential of a novel monoclonal antibody directed against antigenic site B of the hemagglutinin of influenza A viruses", PLOS Pathogens, 5(3):e1000350 (2009).
Tate, et al., "Specific sites of N-linked glycosylation on the hemagglutinin of H1N1 subtype influenza A virus determine sensitivity to inhibitors of the innate immune system and virulence in mice", The Journal of Immunology, 187(4):1184-1894 (2011).
Whittle, et al., "Broadly neutralizing human antibody that recognizes the receptor-binding pocket of influenza virus hemagglutinin", Proceedings, National of Academy Sciences, 108(34):14216-14221 (2011).
Arnold, et al., "The Swiss-Model Workspace: A Web-Based Environment for Protein Structure Homology Modelling", Bioinformatics 22:195-201 (2006).
Barbey-Martin, et al., "An Antibody That Prevents the Hemagglutinin Low pH Fusogenic Transition", Virology 294:70-74 (2002).
Beyer, et al., "Comparison of Serology and Reactogenicity between Influenza Subunit Vaccines and Whole Virus or Split Vaccines A Review and Meta-Analysis of the Literature", Clin Drug Invest 15:(1)1-12 (1998).
Bioedit Sequence Alignment Editor http://www.mbio.ncsu.edu/bioedit/bioedit.html (1999).
Bizebard, et al., "Structure of Influenza Virus Haemagglutinin Complexed With a Neutralizing Antibody", Nature 376:92-94 (1995).
Budowsky, et al., "Principles of Selective Inactivation of Viral Genome. VI. Inactivation of the Infectivity of the Influenza Virus by the Action of βI-Propiolactone", Vaccine 9:398-402 (1991).
Carney, et al., "Flexible Label-Free Quantitative Assay for Antibodies to Influenza Virus Hemagglutinins", Clin Vaccine Immunol17:1407-1416 (2010).
Cattoli, et al., "Antigenic Drift in H5N1 Avian Influenza Virus in Poultry Is Driven by Mutations in Major Antigenic Sites of the Hemagglutinin Molecule Analogous to Those for Human Influenza Virus", J Virol 85:8718-8724 (2011).
CHMP/BWP/214/96, Guideline on Dossier Structure and Content for Pandemic Influenza Vaccine Marketing Authorization Application (2008).
Davis, et al., "Molprobity: All-Atom Contacts and Structure Validation for Proteins and Nucleic Acids", Nucleic Acids Res 35:W375-W383 (2007).
Delano http://www.pymol.org (2002).
Ekiert, et al., "Antibody Recognition of a Highly Conserved Influenza Virus Epitope", Science 324:246-251 (2009).
Emsley, et al., "Features and development of Coot", Acta Crystallogr D Biol Crystallogr 66:486-501 (2010).
Fleury, et al., "A Complex of Influenza Hemagglutinin With a Neutralizing Antibody That Binds Outside the Virus Receptor Binding Site", Nat Struct Biol 6:530-534 (1999).
Fleury, et al., "Structural Evidence for Recognition of a Single Epitope by Two Distinct Antibodies", Proteins 40:572-578 (2000).
Fouchier, et al., "Characterization of a Novel Influenza a Virus Hemagglutinin Subtype (H16) Obtained from Black-Headed Gulls", J. Virol 79:2814-2822 (2005).
Gerhard, et al., "Antigenic Structure of Influenza Virus Haemagglutinin Defined by Hybridoma Antibodies", Nature 290:713-717 (1981).
Hossain, et al., "Virus-Like Particle Vaccine Containing Hemagglutinin Confers Protection against 2009 H1N1 Pandemic Influenza", Clin Vaccine Immunol 18:2010-2017 (2011).
Kaiser, "A One-Size-Fits-All Flu Vaccine?" Science 312:380-382 (2006).
Knossow, et al., "Mechanism of Neutralization of Influenza Virus Infectivity by Antibodies", Virology 302:294-298 (2002).
Krissinel, et al., "Inference of Macromolecular Assemblies from Crystalline State", J Mol Biol 372:774-797 (2007).
McCoy, et al., "Phaser crystallographic software", J Appl Crystallogr 40:658-674 (2007).
Murshudov, et al., "Refinement of Macromolecular Structures by the Maximum-Likelihood Method", Acta Crystallogr D Biol 53:240-253 (1997).
Mylvaganam, et al., "Structural Basis for the Binding of an Anti-cytochrome c Antibody to its Antigen: Crystal Structures of FabE8-Cytochrome c Complex to 1.8 Å Resolution and FabE8 to 2.26 Å Resolution", J Mol Biol 281:301-322 (1998).
Nettleship, et al., "A Pipeline for the Production of Antibody Fragments for Structural Studies Using Transient Expression in Hek 293t Cells", Protein Expr Purif 62:83-89 (2008).
Okuno, et al., "A Common Neutralizing Epitope Conserved Between the Hemagglutinins of Influenza A Virus H1 and H2 Strains", J Virol 67:2552-2558 (1993).
Okuno, et al., "Protection against the Mouse-Adapted A/FM/1/47 Strain of Influenza A Virus in Mice by a Monoclonal Antibody with Cross-Neutralizing Activity among Hi and H2 Strains", J Virol 68: 517-520 (1994).
O'Neill et al., "Generation and Characterization of Candidate Vaccine Viruses for Prepandemic Influenza Vaccines", Curr Top Microbiol Immunol 333: 83-107 (2009).
Otwinowski, et al., "Processing of X-Ray Diffraction Data Collected in Oscillation Mode", Methods in Enzymology 276:307-326 (1997).
Reynolds, et al., "Protorp: A Protein-Protein Interaction Analysis Server", Bioinformatics 25:413-414 (2009).
Rowe, et al., "Detection of Antibody to Avian Influenza A (H5N1) Virus in Human Serum by Using a Combination of Serologic Assays", J Clin Microbiol 37:937-943 (1999).
Russell, et al., "The Structure of H5N1 Avian Influenza Neuraminidase Suggests New Opportunities for Drug Design", Nature 443:45-49 (2006).
Smirnov, et al., "Prevention and Treatment of Bronchopneumonia in Mice Caused by Mouse-Adapted Variant of Avian H5N2 Influenza A Virus Using Monoclonal Antibody Against Conserved Epitope in the HA Stem Region", Arch Virol 145:1733-1741 (2000).
Steel, et al., "Influenza Virus Vaccine Based on the Conserved Hemagglutinin Stalk Domain", MBio, 1:1-9 (2010).
Stevens, et al., "Structure and Receptor Specificity of the Hemagglutinin from an H5N1 Influenza Virus", Science 312:404-410 (2006).
Stevens, et al., "Structure of the Uncleaved Human H1 Hemagglutinin from the Extinct 1918 Influenza Virus", Science 303:1866-1870 (2004).
Throsby, et al., "Heterosubtypic Neutralizing Monoclonal Antibodies Cross-Protective against H5N1 and H1N1 Recovered from Human IgM+ Memory B Cells", PLoS One 3:e3942, pp. 1-14 (2008).
Whittle, et al., "Broadly Neutralizing Human Antibody That Recognizes the Receptor-Binding Pocket of Influenza Virus Hemagglutinin", PNAS 108:14216-14221 (2011).
Wiley, et al., "Structural Identification of the Antibody-Binding Sites of Hong Kong Influenza Haemagglutinin and Their Involvement in Antigenic Variation", Nature 289:373-378 (1981).
Wiley, et al., "The Structure and Function of the Hemagglutinin Membrane Glycoprotein of Influenza Virus", Ann. Rev. Biochem 56:365-394 (1987).
Wilson, et al., "Antibody-Antigen Interactions: New Structures and New Conformational Changes", Curr Opin Struct Biol 4:857-867 (1994).
Wood et al., "International Collaborative Study of Single-Radial-Diffusion and Immunoelectrophoresis Techniques for the Assay of Haemagglutinin Antigen of Influenza" Virus J. Biol. Stand 9:317-330 (1981).
Wood, et al., "An Improved Single-Radial-Immunodiffusion Technique for the Assay of Influenza Haemagglutinin Antigen: Application for Potency Determinations of Inactivated Whole Virus and Subunit Vaccines", J. Biol. Stand 5:237-247 (1977).
Xu, et al., "Structural Basis of Preexisting Immunity to the 2009 H1N1 Pandemic Influenza Virus", Science 328:357-360 (2010).
Yang, et al., "Structure and Receptor Binding Properties of a Pandemic H1 Virus Hemagglutinin", Current Topics in Microbiology and Immunology, PLoS Curr 2 RRN1152 (2012).

(56) References Cited

OTHER PUBLICATIONS

Yang, et al., "Structures of Receptor Complexes of a North American H7N2 Influenza Hemagglutinin with a Loop Deletion in the Receptor Binding Site", PLoS Pathog 6 e1001081 (2010).

Zhu, et al., "Direct Observation of an Enamine Intermediate in Amine Catalysis" J Am Chem Soc 131:18206-18207 (2009).

* cited by examiner

Figure 7a

Hemagglutination-Inhibition

| Antibody | Virus | | | | |
|---|---|---|---|---|---|
| | VN/1203 | Anhui/05 | Indo/05 | Pheasant/NJ | Brisbane/59 |
| 1A2 IgG | - | 16 | - | - | - |
| 1A2 Fab2' | - | - | - | - | - |
| 1A2 Fab | - | - | - | - | - |
| 5C5 IgG | 128 | 64 | 64 | 64 | - |
| 5C5 Fab2' | 64 | 32 | 64 | 32 | - |
| 5C5 Fab | 128 | - | - | - | - |

Figure 7b

Microneutralization

| Antibody | Virus | | | | |
|---|---|---|---|---|---|
| | VN/1203 | Anhui/05 | Indo/05 | Pheasant/NJ | Brisbane/59 |
| 1A2 IgG | 128 | 512 | 1024 | 512 | <16 |
| 1A2 Fab2' | 64 | 256 | 1024 | 512 | <16 |
| 1A2 Fab | <16 | <16 | <16 | <16 | <16 |
| 5C5 IgG | 16,400 | 256 | 36,800 | 36,800 | <16 |
| 5C5 Fab2' | 8,200 | 256 | 2,048 | 36,800 | <16 |
| 5C5 Fab | 512 | <16 | 32 | 512 | <16 |

Figure 8

SEQUENCE LISTING

<160> NUMBER OF SEQ ID NOS: 56

<210> SEQ ID NO 1
<211> LENGTH: 552
<212> TYPE: PRT
<213> ORGANISM: Influenza virus
<220> FEATURE:
<223> OTHER INFORMATION: Influenza A/Vietnam/1203/04 virus

<400> SEQUENCE: 1

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Lys His Asn Gly Lys Leu Cys Asp Leu Asp Gly Val Lys
35 40 45

```
Pro Leu Ile Leu Arg Asp Cys Ser Val Ala Gly Trp Leu Leu Gly Asn
 50                  55                  60

Pro Met Cys Asp Glu Phe Ile Asn Val Pro Glu Trp Ser Tyr Ile Val
 65                  70                  75                  80

Glu Lys Ala Asn Pro Val Asn Asp Leu Cys Tyr Pro Gly Asp Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
```

```
                465                 470                 475                 480
Ser Val Arg Asn Gly Thr Tyr Asp Tyr Pro Gln Tyr Ser Glu Glu Ala
                    485                 490                 495

Arg Leu Lys Arg Glu Glu Ile Ser Gly Val Lys Leu Glu Ser Ile Gly
                500                 505                 510

Ile Tyr Gln Ile Leu Ser Ile Tyr Ser Thr Val Ala Ser Ser Leu Ala
            515                 520                 525

Leu Ala Ile Met Val Ala Gly Leu Ser Leu Trp Met Cys Ser Asn Gly
        530                 535                 540

Ser Leu Gln Cys Arg Ile Cys Ile
545                 550

<210> SEQ ID NO 2
<211> LENGTH: 123
<212> TYPE: PRT
<213> ORGANISM: Mus sp.

<400> SEQUENCE: 2

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Phe
            20                  25                  30

Ile Met Tyr Trp Val Lys Gln Lys Pro Gly Gln Gly Leu Glu Trp Leu
        35                  40                  45

Gly Tyr Ile Asp Pro Tyr Asn Asp Gly Thr Lys Tyr Asn Glu Lys Phe
    50                  55                  60

Glu Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Arg Gly Asn Tyr Gly Asn Gly Phe Ala Tyr Trp Gly Gln Gly
            100                 105                 110

Thr Leu Val Thr Val Ser Ala Ala Lys Thr Ser
        115                 120

<210> SEQ ID NO 3
<211> LENGTH: 114
<212> TYPE: PRT
<213> ORGANISM: Mus sp.

<400> SEQUENCE: 3

Asp Ile Val Met Thr Gln Ser Gln Lys Phe Val Ser Thr Ser Val Gly
1               5                   10                  15

Asp Arg Val Ser Val Thr Cys Lys Ala Ser Gln Asn Val Gly Ser Asn
            20                  25                  30

Val Ala Trp Tyr Gln His Lys Pro Gly His Ser Pro Thr Ala Leu Ile
        35                  40                  45

Tyr Ser Ala Ser His Arg Tyr Ser Gly Val Pro Asp Arg Phe Thr Gly
    50                  55                  60

Ser Glu Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ser Tyr Pro Tyr
                85                  90                  95

Thr Phe Gly Gly Gly Thr Lys Leu Glu Ile Lys Arg Ala Asp Ala Ala
            100                 105                 110

Pro Thr
```

```
<210> SEQ ID NO 4
<211> LENGTH: 126
<212> TYPE: PRT
<213> ORGANISM: Mus sp.

<400> SEQUENCE: 4

Gln Val Gln Leu Gln Gln Ser Gly Ala Glu Leu Val Arg Pro Gly Thr
 1               5                  10                  15

Ser Val Lys Ile Ser Cys Lys Ala Ser Gly Tyr Ala Phe Ser Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Ser Gly Asn Asn His Tyr Asn Glu Lys Phe
        50                  55                  60

Lys Gly Lys Ala Thr Leu Thr Ala Asp Lys Ser Ser Arg Thr Val Tyr
 65                 70                  75                  80

Met Gln Leu Ser Ser Leu Thr Ser Glu Asp Ser Ser Val Tyr Phe Cys
                85                  90                  95

Thr Arg Gly Pro Ile Phe Thr Thr Ala Trp Phe Ala Tyr Trp Gly Gln
                100                 105                 110

Gly Thr Leu Val Thr Val Ser Ala Ala Gln Lys Gln Thr Trp
            115                 120                 125

<210> SEQ ID NO 5
<211> LENGTH: 114
<212> TYPE: PRT
<213> ORGANISM: Mus sp.

<400> SEQUENCE: 5

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Asp Thr Tyr
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
 65                 70                  75                  80

Glu Asp Leu Ala Glu Tyr Phe Cys Gln Gln Tyr Lys Thr Tyr Pro Phe
                85                  90                  95

Thr Phe Gly Ser Gly Thr Lys Leu Glu Ile Lys Arg Ala Asp Ala Ala
                100                 105                 110

Pro Thr

<210> SEQ ID NO 6
<211> LENGTH: 10
<212> TYPE: PRT
<213> ORGANISM: Mus sp.

<400> SEQUENCE: 6

Gly Tyr Thr Phe Thr Ser Phe Ile Met Tyr
 1               5                  10

<210> SEQ ID NO 7
<211> LENGTH: 15
<212> TYPE: PRT
```

```
<213> ORGANISM: Mus sp.

<400> SEQUENCE: 7

Asp Pro Tyr Asn Asp Gly Thr Lys Tyr Asn Glu Lys Phe Glu Gly
1               5                   10                  15

<210> SEQ ID NO 8
<211> LENGTH: 10
<212> TYPE: PRT
<213> ORGANISM: Mus sp.

<400> SEQUENCE: 8

Arg Gly Asn Tyr Gly Asn Gly Phe Ala Tyr
1               5                   10

<210> SEQ ID NO 9
<211> LENGTH: 11
<212> TYPE: PRT
<213> ORGANISM: Mus sp.

<400> SEQUENCE: 9

Lys Ala Ser Gln Asn Val Gly Ser Asn Val Ala
1               5                   10

<210> SEQ ID NO 10
<211> LENGTH: 7
<212> TYPE: PRT
<213> ORGANISM: Mus sp.

<400> SEQUENCE: 10

Ser Ala Ser His Arg Tyr Ser
1               5

<210> SEQ ID NO 11
<211> LENGTH: 9
<212> TYPE: PRT
<213> ORGANISM: Mus sp.

<400> SEQUENCE: 11

Gln Gln Tyr Tyr Ser Tyr Pro Tyr Thr
1               5

<210> SEQ ID NO 12
<211> LENGTH: 200
<212> TYPE: PRT
<213> ORGANISM: Influenza virus

<400> SEQUENCE: 12

Leu Cys Lys Leu Lys Gly Ile Ala Pro Leu Gln Leu Gly Lys Cys Asn
1               5                   10                  15

Ile Ala Gly Trp Leu Leu Gly Asn Pro Glu Cys Asp Leu Leu Leu Thr
                20                  25                  30

Ala Ser Ser Trp Ser Tyr Ile Val Glu Thr Ser Asn Ser Glu Asn Gly
            35                  40                  45

Thr Cys Tyr Pro Gly Asp Phe Ile Asp Tyr Glu Glu Leu Arg Glu Gln
        50                  55                  60

Leu Ser Ser Val Ser Ser Phe Glu Lys Phe Glu Ile Phe Pro Lys Thr
65                  70                  75                  80

Ser Ser Trp Pro Asn His Glu Thr Thr Lys Gly Val Thr Ala Ala Cys
                85                  90                  95

Ser Tyr Ala Gly Ala Ser Ser Phe Tyr Arg Asn Leu Leu Trp Leu Thr
                100                 105                 110
```

```
Lys Lys Gly Ser Ser Tyr Pro Lys Leu Ser Lys Ser Tyr Val Asn Asn
        115                 120                 125

Lys Gly Lys Glu Val Leu Val Leu Trp Gly Val His His Pro Pro Thr
    130                 135                 140

Gly Thr Asp Gln Gln Ser Leu Tyr Gln Asn Ala Asp Ala Tyr Val Ser
145                 150                 155                 160

Val Gly Ser Ser Lys Tyr Asn Arg Arg Phe Thr Pro Glu Ile Ala Ala
                165                 170                 175

Arg Pro Lys Val Arg Asp Gln Ala Gly Arg Met Asn Tyr Tyr Trp Thr
            180                 185                 190

Leu Leu Glu Pro Gly Asp Thr Ile
        195                 200

<210> SEQ ID NO 13
<211> LENGTH: 199
<212> TYPE: PRT
<213> ORGANISM: Influenza virus

<400> SEQUENCE: 13

Leu Cys Leu Leu Lys Gly Ile Ala Pro Leu Gln Leu Gly Asn Cys Ser
1               5                   10                  15

Val Ala Gly Trp Ile Leu Gly Asn Pro Glu Cys Glu Leu Leu Ile Ser
            20                  25                  30

Lys Glu Ser Trp Ser Tyr Ile Val Glu Lys Pro Asn Pro Glu Asn Gly
        35                  40                  45

Thr Cys Tyr Pro Gly His Phe Ala Asp Tyr Glu Glu Leu Arg Glu Gln
    50                  55                  60

Leu Ser Ser Val Ser Ser Phe Glu Arg Phe Glu Ile Phe Pro Lys Glu
65                  70                  75                  80

Ser Ser Trp Pro Asn His Thr Val Thr Gly Val Ser Ala Ser Cys Ser
                85                  90                  95

His Asn Gly Glu Ser Ser Phe Tyr Arg Asn Leu Leu Trp Leu Thr Gly
            100                 105                 110

Lys Asn Gly Leu Tyr Pro Asn Leu Ser Lys Ser Tyr Ala Asn Asn Lys
        115                 120                 125

Glu Lys Glu Val Leu Val Leu Trp Gly Val His His Pro Pro Asn Ile
    130                 135                 140

Gly Asp Gln Lys Ala Leu Tyr His Thr Glu Asn Ala Tyr Val Ser Val
145                 150                 155                 160

Val Ser Ser His Tyr Ser Arg Lys Phe Thr Pro Glu Ile Ala Lys Arg
                165                 170                 175

Pro Lys Val Arg Asp Gln Glu Gly Arg Ile Asn Tyr Tyr Trp Thr Leu
            180                 185                 190

Leu Glu Pro Gly Asp Thr Ile
        195

<210> SEQ ID NO 14
<211> LENGTH: 199
<212> TYPE: PRT
<213> ORGANISM: Influenza virus

<400> SEQUENCE: 14

Leu Cys Asp Leu Asp Gly Val Lys Pro Leu Ile Leu Arg Asp Cys Ser
1               5                   10                  15

Val Ala Gly Trp Leu Leu Gly Asn Pro Met Cys Asp Glu Phe Ile Asn
            20                  25                  30
```

```
Val Pro Glu Trp Ser Tyr Ile Val Glu Lys Ala Asn Pro Val Asn Asp
        35                  40                  45

Leu Cys Tyr Pro Gly Asp Phe Asn Asp Tyr Glu Glu Leu Lys His Leu
 50                  55                  60

Leu Ser Arg Ile Asn His Phe Glu Lys Ile Gln Ile Ile Pro Lys Ser
 65                  70                  75                  80

Tyr Trp Ser Ser His Glu Ala Ser Leu Gly Val Ser Ser Ala Cys Pro
                     85                  90                  95

Tyr Gln Gly Lys Ser Ser Phe Phe Arg Asn Val Val Trp Leu Ile Lys
                100                 105                 110

Lys Asn Ser Thr Tyr Pro Thr Ile Lys Arg Ser Tyr Asn Asn Thr Asn
                115                 120                 125

Gln Glu Asp Leu Leu Val Leu Trp Gly Ile His His Pro Asn Asp Ala
            130                 135                 140

Ala Glu Gln Thr Lys Leu Tyr Gln Asn Pro Thr Thr Tyr Ile Ser Val
145                 150                 155                 160

Gly Thr Ser Thr Leu Asn Gln Arg Leu Val Pro Arg Ile Ala Thr Arg
                    165                 170                 175

Ser Lys Val Asn Gly Gln Ser Gly Arg Met Glu Phe Phe Trp Thr Ile
                180                 185                 190

Leu Lys Pro Asn Asp Ala Ile
        195

<210> SEQ ID NO 15
<211> LENGTH: 8
<212> TYPE: PRT
<213> ORGANISM: Influenza virus

<400> SEQUENCE: 15

Glu Ala Ser Leu Gly Val Ser Ser
1               5

<210> SEQ ID NO 16
<211> LENGTH: 8
<212> TYPE: PRT
<213> ORGANISM: Influenza virus

<400> SEQUENCE: 16

Glu Ala Ser Ser Gly Val Ser Ser
1               5

<210> SEQ ID NO 17
<211> LENGTH: 8
<212> TYPE: PRT
<213> ORGANISM: Influenza virus

<400> SEQUENCE: 17

Glu Ala Ser Ser Gly Val Ser Ala
1               5

<210> SEQ ID NO 18
<211> LENGTH: 8
<212> TYPE: PRT
<213> ORGANISM: Influenza virus

<400> SEQUENCE: 18

Glu Ala Ser Ser Gly Val Ser Ser
1               5
```

```
<210> SEQ ID NO 19
<211> LENGTH: 7
<212> TYPE: PRT
<213> ORGANISM: Influenza virus

<400> SEQUENCE: 19

Glu Ala Ser Gly Val Ser Ser
1               5

<210> SEQ ID NO 20
<211> LENGTH: 8
<212> TYPE: PRT
<213> ORGANISM: Influenza virus

<400> SEQUENCE: 20

Asp Ala Ser Ser Gly Val Ser Ser
1               5

<210> SEQ ID NO 21
<211> LENGTH: 5
<212> TYPE: PRT
<213> ORGANISM: Influenza virus

<400> SEQUENCE: 21

Ile Lys Lys Asn Ser
1               5

<210> SEQ ID NO 22
<211> LENGTH: 5
<212> TYPE: PRT
<213> ORGANISM: Influenza virus

<400> SEQUENCE: 22

Ile Lys Lys Asn Ser
1               5

<210> SEQ ID NO 23
<211> LENGTH: 5
<212> TYPE: PRT
<213> ORGANISM: Influenza virus

<400> SEQUENCE: 23

Ile Lys Lys Asp Asn
1               5

<210> SEQ ID NO 24
<211> LENGTH: 5
<212> TYPE: PRT
<213> ORGANISM: Influenza virus

<400> SEQUENCE: 24

Ile Lys Lys Asn Asn
1               5

<210> SEQ ID NO 25
<211> LENGTH: 5
<212> TYPE: PRT
<213> ORGANISM: Influenza virus

<400> SEQUENCE: 25

Thr Lys Lys Asp Asn
1               5

<210> SEQ ID NO 26
<211> LENGTH: 5
```

<212> TYPE: PRT
<213> ORGANISM: Influenza virus

<400> SEQUENCE: 26

Ile Lys Lys Asn Asn
1               5

<210> SEQ ID NO 27
<211> LENGTH: 5
<212> TYPE: PRT
<213> ORGANISM: Influenza virus

<400> SEQUENCE: 27

Asn Asp Ala Ala Glu
1               5

<210> SEQ ID NO 28
<211> LENGTH: 5
<212> TYPE: PRT
<213> ORGANISM: Influenza virus

<400> SEQUENCE: 28

Asn Asp Ala Ala Glu
1               5

<210> SEQ ID NO 29
<211> LENGTH: 5
<212> TYPE: PRT
<213> ORGANISM: Influenza virus

<400> SEQUENCE: 29

Asn Asp Glu Ala Glu
1               5

<210> SEQ ID NO 30
<211> LENGTH: 5
<212> TYPE: PRT
<213> ORGANISM: Influenza virus

<400> SEQUENCE: 30

Asn Asp Ala Ala Glu
1               5

<210> SEQ ID NO 31
<211> LENGTH: 5
<212> TYPE: PRT
<213> ORGANISM: Influenza virus

<400> SEQUENCE: 31

Asn Asp Ala Ala Glu
1               5

<210> SEQ ID NO 32
<211> LENGTH: 5
<212> TYPE: PRT
<213> ORGANISM: Influenza virus

<400> SEQUENCE: 32

Asn Asp Ala Ala Glu
1               5

<210> SEQ ID NO 33
<211> LENGTH: 4
<212> TYPE: PRT
<213> ORGANISM: Influenza virus
<210> SEQ ID NO 34
<211> LENGTH: 4
<212> TYPE: PRT
<213> ORGANISM: Influenza virus

<400> SEQUENCE: 34

Asp Gly Val Lys
1

<210> SEQ ID NO 35
<211> LENGTH: 4
<212> TYPE: PRT
<213> ORGANISM: Influenza virus

<400> SEQUENCE: 35

Asn Gly Val Lys
1

<210> SEQ ID NO 36
<211> LENGTH: 4
<212> TYPE: PRT
<213> ORGANISM: Influenza virus

<400> SEQUENCE: 36

Asp Gly Val Lys
1

<210> SEQ ID NO 37
<211> LENGTH: 4
<212> TYPE: PRT
<213> ORGANISM: Influenza virus

<400> SEQUENCE: 37

Asp Gly Val Lys
1

<210> SEQ ID NO 38
<211> LENGTH: 4
<212> TYPE: PRT
<213> ORGANISM: Influenza virus

<400> SEQUENCE: 38

Ser Gly Val Arg
1

<210> SEQ ID NO 39
<211> LENGTH: 5
<212> TYPE: PRT
<213> ORGANISM: Influenza virus

<400> SEQUENCE: 39

Ile Asn Val Pro Glu
1               5

<210> SEQ ID NO 40
<211> LENGTH: 5
<212> TYPE: PRT
<213> ORGANISM: Influenza virus

<400> SEQUENCE: 40

Ile Asn Val Pro Glu
1               5

<210> SEQ ID NO 41
<211> LENGTH: 5
<212> TYPE: PRT
<213> ORGANISM: Influenza virus

<400> SEQUENCE: 41

Ile Asn Val Pro Glu
1               5

<210> SEQ ID NO 42
<211> LENGTH: 5
<212> TYPE: PRT
<213> ORGANISM: Influenza virus

<400> SEQUENCE: 42

Ile Asn Val Pro Glu
1               5

<210> SEQ ID NO 43
<211> LENGTH: 5
<212> TYPE: PRT
<213> ORGANISM: Influenza virus

<400> SEQUENCE: 43

Leu Asn Val Pro Glu
1               5

<210> SEQ ID NO 44
<211> LENGTH: 5
<212> TYPE: PRT
<213> ORGANISM: Influenza virus

<400> SEQUENCE: 44

Leu Asn Val Pro Glu
1               5

<210> SEQ ID NO 45
<211> LENGTH: 7
<212> TYPE: PRT
<213> ORGANISM: Influenza virus

<400> SEQUENCE: 45

His Phe Glu Lys Ile Gln Ile
1               5

<210> SEQ ID NO 46
<211> LENGTH: 7
<212> TYPE: PRT
<213> ORGANISM: Influenza virus

<400> SEQUENCE: 46

His Phe Glu Lys Ile Gln Ile
1               5

<210> SEQ ID NO 47
<211> LENGTH: 7
<212> TYPE: PRT
<213> ORGANISM: Influenza virus

<400> SEQUENCE: 47

His Phe Glu Lys Ile Gln Ile

```
1               5

<210> SEQ ID NO 48
<211> LENGTH: 7
<212> TYPE: PRT
<213> ORGANISM: Influenza virus

<400> SEQUENCE: 48

His Phe Glu Lys Ile Gln Ile
1               5

<210> SEQ ID NO 49
<211> LENGTH: 7
<212> TYPE: PRT
<213> ORGANISM: Influenza virus

<400> SEQUENCE: 49

His Phe Glu Lys Ile Gln Ile
1               5

<210> SEQ ID NO 50
<211> LENGTH: 7
<212> TYPE: PRT
<213> ORGANISM: Influenza virus

<400> SEQUENCE: 50

His Phe Glu Lys Ile Gln Ile
1               5

<210> SEQ ID NO 51
<211> LENGTH: 4
<212> TYPE: PRT
<213> ORGANISM: Influenza virus

<400> SEQUENCE: 51

Thr Asn Gln Glu
1

<210> SEQ ID NO 52
<211> LENGTH: 4
<212> TYPE: PRT
<213> ORGANISM: Influenza virus

<400> SEQUENCE: 52

Thr Asn Gln Glu
1

<210> SEQ ID NO 53
<211> LENGTH: 4
<212> TYPE: PRT
<213> ORGANISM: Influenza virus

<400> SEQUENCE: 53

Thr Asn Gln Glu
1

<210> SEQ ID NO 54
<211> LENGTH: 4
<212> TYPE: PRT
<213> ORGANISM: Influenza virus

<400> SEQUENCE: 54

Thr Asn Gln Glu
1
```

```
<210> SEQ ID NO 55
<211> LENGTH: 4
<212> TYPE: PRT
<213> ORGANISM: Influenza virus

<400> SEQUENCE: 55

Thr Asn Gln Glu
1

<210> SEQ ID NO 56
<211> LENGTH: 4
<212> TYPE: PRT
<213> ORGANISM: Influenza virus

<400> SEQUENCE: 56

Thr Asn Val Glu
1
```

INFLUENZA ANTIGENS AND ANTIBODIES

This application is a 35 U.S.C. § 371 national stage application of International Application No. PCT/EP2014/068108, filed Aug. 26, 2014, which claims benefit of the filing date of U.S. Provisional Application No. 61/870,862, filed Aug. 28, 2013, which is incorporated herein by reference in its entirety.

GOVERNMENT RIGHTS

This invention was created in the performance of a Cooperative Research and Development Agreement with the Centers for Disease Control and Prevention, an Agency of the Department of Health and Human Services. The Government of the United States has certain rights in this invention. The Centers for Disease Control and Prevention and GlaxoSmithKline Biologicals SA, the parties to Cooperative Research and Development Agreement NCRID-08-317-00, contributed to this joint invention.

SEQUENCE LISTING

The instant application contains a Sequence Listing which has been submitted electronically in ASCII format and is hereby incorporated by reference in its entirety. Said ASCII copy, created on Aug. 16, 2017, is named VB65547_SL.txt and is 20,623 bytes in size.

TECHNICAL FIELD

The present invention relates to novel influenza antigens, novel immunogenic or vaccine compositions, as well as to uses of and to methods for producing said antigens and compositions. In particular, the invention relates to modified forms of haemagglutinin (HA) which, upon use as an antigen, are capable of directing immune responses to genetically more conserved regions of HA. Furthermore, antibodies that bind such regions and uses of such antibodies are provided.

BACKGROUND OF THE INVENTION

Influenza viruses are one of the most ubiquitous viruses present in the world, affecting both humans and livestock. Influenza results in an economic burden, morbidity and even mortality, which are significant. There are three types of influenza viruses: A, B and C.

The influenza virus is an enveloped virus which consists basically of an internal nucleocapsid or core of RNA associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two predominant surface antigens, the glycoproteins HA and neuraminidase (NA), which appear as spikes at the surface of the particles. It is these surface proteins, particularly HA, that determine the antigenic specificity of the influenza subtypes.

Virus strains are classified according to host species of origin, geographic site and year of isolation, serial number, and, for influenza A, by serological properties of subtypes of HA and NA. 16 HA subtypes (H1-H16) and nine NA subtypes (N1-N9) have been identified for influenza A viruses (Webster et al. (1992) Microbiol. Rev. 56:152; Fouchier et al. (2005) J. Virol. 79:2814). Viruses of all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

Influenza A-type viruses evolve and undergo antigenic variability continuously (Wiley and Skehel (1987) Ann. Rev. Biochem. 56:365). A lack of effective proofreading by the viral RNA polymerase leads to a high rate of transcription errors that can result in amino-acid substitutions in surface glycoproteins.

Vaccination plays a critical role in controlling influenza epidemics. Because of the antigenic variability, patients must receive an annual vaccination against the influenza viruses that are predicted on the basis of viral surveillance data to gain immunity against viruses in circulation.

It would of interest to have an influenza vaccine which would not be restricted by inherent strain-specificity, but which would provide a broad protection against a large spectrum of influenza strains. Such a "universal" influenza vaccine could potentially be made by making use of conserved, evolutionarily-stable, epitopes. It has been proposed to make such universal vaccines by using the highly conserved M2 and NP proteins as antigens (Kaiser (2006) Science 312:380). However, these proteins are not abundant on the surface of virions and responses against M2 and NP are much weaker than those induced by standard seasonal vaccines.

HA is abundant on the surface of influenza virions and is the main target of the immune response against the standard vaccines, such as split vaccines. However, the HA molecule is highly variant, and the immune response to HA is predominantly against the more variable regions. Thus, upon influenza vaccination or infection, the immune response is mainly directed at a limited number of continuously evolving, strain-specific, HA antigenic determinants, resulting in very limited cross-reactivity.

Steel et al. (2010, MBio, 1:1) have described an influenza virus vaccine based on the conserved HA stalk domain. However, antibodies against the head domain are more likely to block infection by interfering with virion binding to host cell sialic acid receptors. Thus, it would be of interest to have a "universal" HA antigen which includes the head domain. WO2012082634 describes amino acid substitutions in HA that reduce the responses to dominant hyper-variable epitopes and thus direct responses more to conserved regions of HA.

However, there is still a need for novel influenza antigens which can induce an immune response which provides broad protection against a large spectrum of influenza strains.

Passive immunization with antibodies is another potential way of combating influenza disease. For example, Okuno et al. (1994, J Virol. 68: 517) have described protection against the mouse-adapted A/FM/1/47 strain of influenza A virus in mice by a monoclonal antibody with cross-neutralizing activity among H1 and H2 strains. Similarly, Smirnov et al. (2000, Arch Virol. 145:1733) have described prevention and treatment of bronchopneumonia in mice caused by mouse-adapted variant of avian H5N2 influenza A virus using monoclonal antibody against conserved epitope in the HA stem region.

However, there is still a need for novel anti-HA antibodies which exhibit neutralizing activity against a broad spectrum of influenza strains.

SUMMARY OF THE INVENTION

The inventors have isolated and characterized monoclonal anti-HA antibodies that are both neutralizing and bind conserved regions in HA, thus allowing binding to HAs from a broad range of influenza strains. These functional properties render the antibodies potentially useful for the treatment and/or prevention of influenza infection and/or disease, even in situations where the strain causing the (potential) infection and/or disease has not been precisely identified.

In addition, the identification of the conserved epitopes to which these antibodies bind enabled the design of modified HA antigens for vaccination, wherein hyper-variable regions of HA are shielded using Asn-linked glycosylation and thus immune responses potentially become directed to more conserved regions of the antigen, thus provided a broader scope of protection.

Accordingly, in a first aspect of the invention, there is provided a modified influenza HA antigen comprising additional Asn-linked glycosylation on at least two surface patches selected from the group of surfaces patches consisting of: Site A, Site B, Site C, Site, D and Site E.

In a further aspect, a polynucleotide encoding a modified HA antigen as described herein is provided.

In a further aspect, an immunogenic composition comprising an antigen as defined herein and a pharmaceutically-acceptable carrier is provided.

In a further aspect, there is provided a method for producing an antigen as defined herein comprising expressing a polynucleotide as defined herein in a eukaryotic cell.

In an even further aspect, there is provided a method of prevention and/or treatment against influenza disease, comprising the administration of an antigen or immunogenic composition as defined herein to a person in need thereof.

In a yet further aspect, there is provided an anti-HA antibody that competes for binding to HA with an antibody comprising a heavy chain comprising the CDR1, CDR2 and CDR3 sequences as set forth in SEQ ID NO: 6, 7 and 8, and a light chain comprising the CDR1, CDR2 and CDR3 sequences as set forth in SEQ ID NO:9, 10 and 11.

BRIEF DESCRIPTION OF THE FIGURES

FIG. 8: Sequence alignment of residues structurally-equivalent to the 5C5 and 1A2 epitopes (HA amino acids buried by Fab binding) of Viet04 across different clades of H5 viruses. A) Residues in the 5C5 epitope. Residues that influence sialic acid specificity (Stevens et al. (2006) Science 312:404) are numbered in red. Amino acid substitutions relative to Viet04 (clade 1) are highlighted. Residues mutated to map the 5C5 and 1A2 epitopes are also depicted, with mutations that diminished binding to below 85% of Wt underlined. B) Equivalent alignment of sequences within the 1A2 epitope. FIG. 8A discloses the sequences at positions 126-133 as SEQ ID NOS: 15-20, the sequences at positions 151-155 as SEQ ID NOS: 21-26, and the sequences at positions 182-186 as SEQ ID NOS: 27-32, all respectively, in order of appearance. FIG. 8B discloses the sequences at positions 45-48 as SEQ ID NOS: 33-38, the sequences at positions 71-75 as SEQ ID NOS: 39-44, the sequences at positions 110-116 as SEQ ID NOS: 45-50, and the sequences at positions 167-170 as SEQ ID NOS: 51-56, all respectively, in order of appearance.

DETAILED DESCRIPTION

Definitions

Figure 1A:
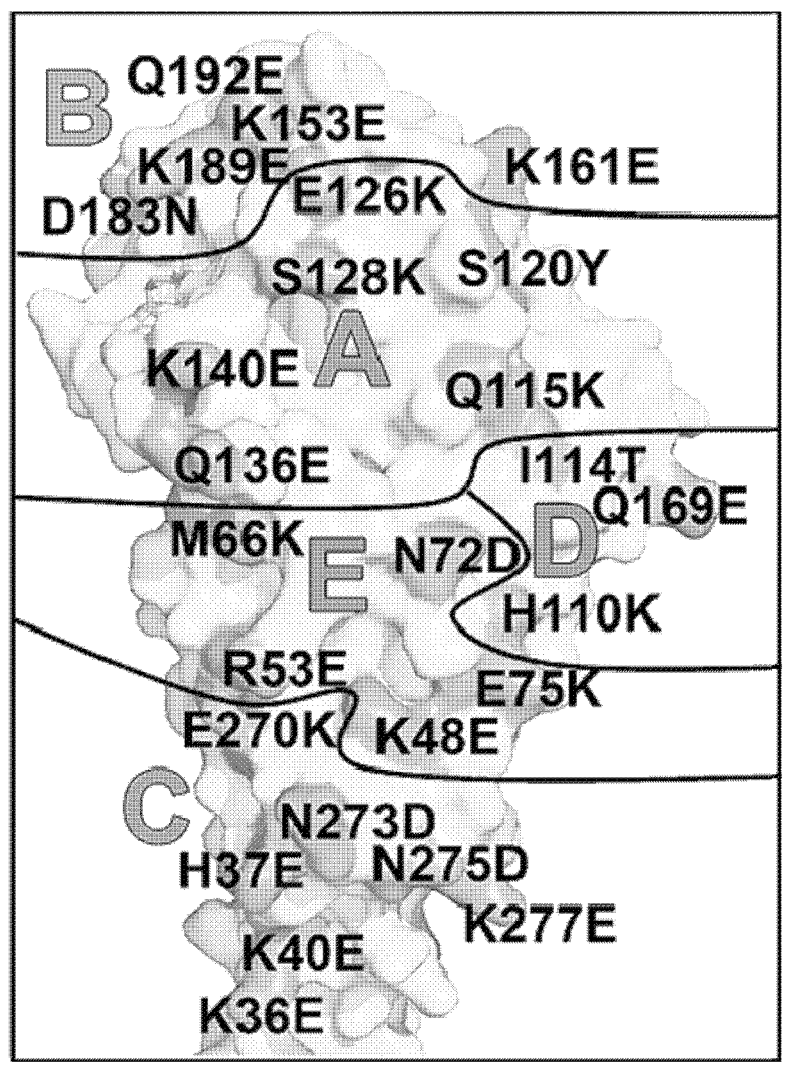
FIG. 1: A) Surface representation of Viet04 H5 HA1, highlighting mutations used for epitope mapping at the surface of HA1 binned into sites A, B, C, D and E, respectively. A single sialic acid moiety is shown within the sialic acid binding site (between D183N and K140E) to illustrate the relative location of the antigenic sites. B) Surface representation of the HA1/HA2 monomer of H5 HA, showing the relative orientation of the HA1, HA2, receptor binding site (RBS) and CHO mutants. HA1 is colored in white, HA2 is grey and Asn residues that have been introduced or modified for additional N-glycosylation (CHO mutants) are colored black.

The term "modified influenza haemagglutinin antigen comprising additional Asn-linked glycosylation" when used herein indicates an HA antigen which contains Asn-linked additional glycosylation as compared to the Asn-linked glycosylation present in HA of most naturally-occurring strains of the given subtype, e.g. for H5 (clade 1.0), most naturally-occurring strains have potential Asn-linked glycosylation at positions 11, 23, 154, 165, 286 (in HA1), as well as 484 (position 154 in HA2).

Typically, the coding sequence for HA of a naturally-occurring strain has been modified to introduce acceptor sites for Asn-linked glycosylation at a position other than 11, 23, 154, 165, 286 or 484. Acceptor sites for Asn-linked glycosylation have the consensus sequence Asn-X-Ser/Thr, wherein X is not Pro. Acceptor sites can be introduced in various ways, including introduction, e.g. by substitution, of an Asn-X-Ser or Asn-X-Thr site in a part of the sequence where none of those residues are present or for example introduction of an Asn codon two codons upstream of an existing Ser or Thr codon, or a Ser or Thr codon two positions downstream of an Asn codon. In a different embodiment, however, the modified HA antigen is an HA antigen isolated from nature, which has additional Asn-linked glycosylation as compared to the Asn-linked glycosylation present in HA of most naturally-occurring strains of the same subtype.

The presence of an acceptor site for Asn-linked glycosylation is required, but not necessarily sufficient for expression of a modified influenza HA antigen comprising additional Asn-linked glycosylation. Some amino-acid substitutions may cause mis-folding and thus prevent functional protein production. Other amino-acid substitutions may allow correct folding, but their structural location may prevent the acceptor site from actually being glycosylated. Techniques for testing production of a functional modified influenza HA antigen comprising additional Asn-linked glycosylation are described in the Examples herein. Alternative techniques have been described in the art.

The term "position corresponding to ### (e.g. 140)" when used herein refers to a position in an HA which is not from A/Vietnam/1203/04, which position in said HA is structurally equivalent to position ### in A/Vietnam/1203/04. "Structurally equivalent" means that the amino-acid residue is similarly positioned relative to the three-dimensional structure of said HA. In some cases, the amino acid number counting from the N-terminus may be the same as in HA from A/Vietnam/1203/04, but in other cases, the number may be different, for example, the number counting from the N-terminus of said HA may be ### minus 3 (e.g. 137), ### minus 2, ### minus 1, ### plus 1, ### plus 2, ### plus 3 (e.g. 143) or a position which is even further removed from ###. Structurally equivalent amino acid residues can be identified using modeling using HA from A/Vietnam/1203/04 as a starting point. The structurally equivalent amino acid residue may be the same as position ### in HA from A/Vietnam/1203/04 or the amino acid residue may be different (e.g. an structurally-equivalent amino acid to Lys 140 of HA of A/Vietnam/1203/04 may be e.g. an Arg at position 141 of said HA).

The term "mature protein" when used herein refers to the ectodomain (i.e. extracellular) component of each polypeptide that is present in the wild-type HA protein at the cell surface. The protein has been produced and processed by the protein synthesis machinery and the signal peptide has been removed. Numbering of the amino acid sequence of the mature protein is consecutive from the amino (N-) terminal to the carboxyl (—C) terminal residue, such that position 1 corresponds to the residue at the N-terminus of each subdomain in the wild type HA as found in virions. As such, any additional engineered residues at the N-terminus, such as those that are introduced as part of the expression strategy or for the purposes of solubilization or purification, are numbered in reverse order (i.e. from —C to N-terminal) from position 1, starting with position 0 (e.g. 0, –1, –2, etc.). Note that consecutive numbering of HA proteins contrasts with other recognized systems for the numbering of HA proteins, such as the "H3" and "H1" numbering systems, which refer to structural relatedness amongst subtypes of HA proteins and do not necessarily number residues in consecutive order.

Figure 4:
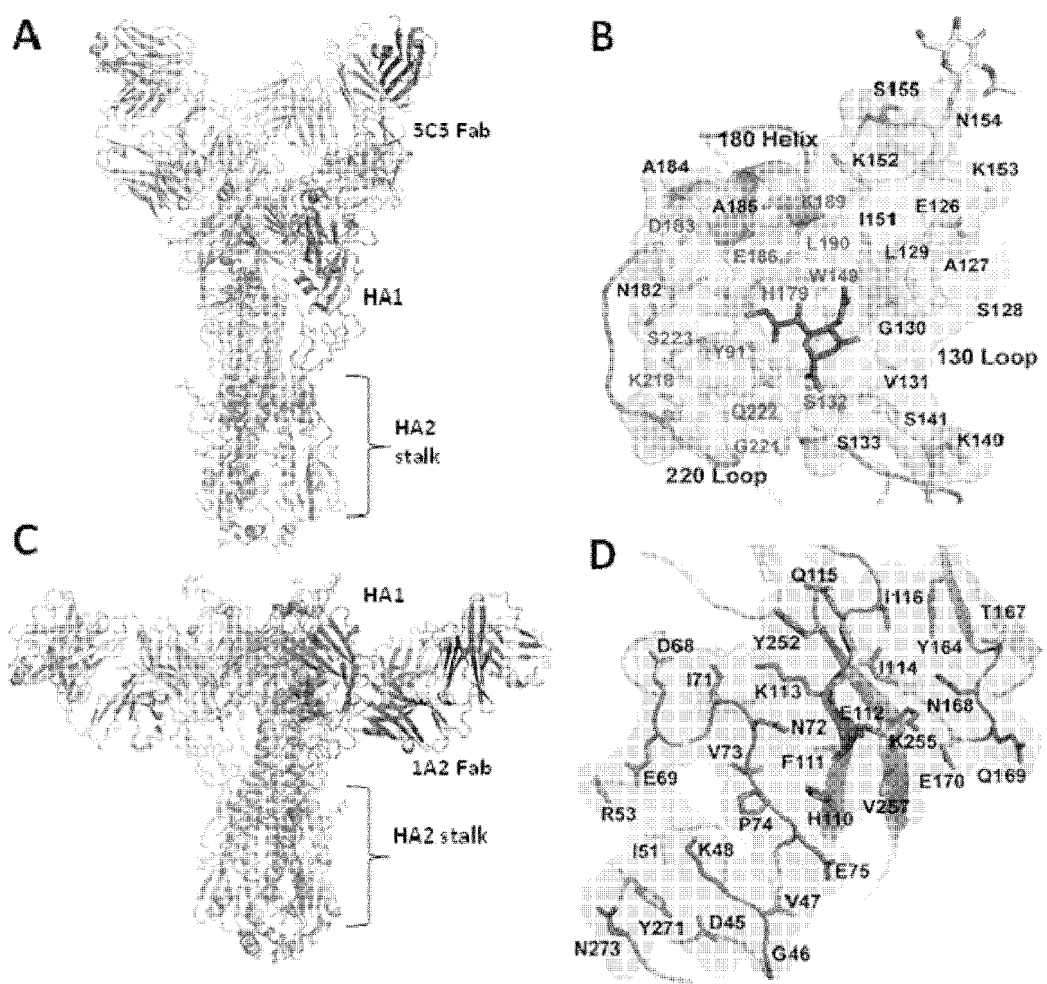
FIG. 4: Crystal structures and epitope footprints of 5C5 Fab and 1A2 Fabs in complex with Viet04 H5 HA. A) Trimeric 5C5 Fab-H5 complex depicted as a cartoon representation. For clarity, a single 5C5 Fab-H5 monomer, HA1 and HA2 are labelled. The other two protomers in the complex are also depicted as a molecular surface representation and N-carbohydrates are depicted as sticks. B) The neutralizing epitope of 5C5. The molecular surface of Viet04 covered by the 5C5 depicted as a surface representation. A sialic acid moiety, modelled in the receptor binding site, illustrates the relative location of the 5C5 epitope. Residues implicated in receptor-specificity of Viet04 (Stevens et al. (2006) Science 312:404) are highlighted. The vicinal N-acetyl glucosamine at Asn158 highlights the proximity of the Ab epitope to the glycosylation site. C) The trimeric 1A2 Fab-H5 complex, depicted as in FIG. 4A. D) The neutralizing epitope of 1A2. The molecular surface of Viet04 covered by the 1A2 is depicted as a surface representation.

The terms "HA1.", "HA1 chain" or "HA1 component" when used herein refer to the region of the HA protein including amino acid residues from approximately 1-330 of the mature haemagglutinin protein. The HA1 chain comprises all residues that are N-terminal to the HA1/HA2 cleavage peptide of the precursor HA0 protein, including the receptor binding domain of the HA protein (see FIGS. 1b and 4).

The terms "HA2", "HA2 chain" or "HA2 component" when used herein refer to the region of the HA protein including amino acid residues from approximately 331-504 of the mature HA0 haemagglutinin polypeptide. Of note, these residues within the HA2 chain are commonly numbered independently of those in HA1, such that HA2 residues may be numbered consecutively 1-174. The HA2 chain comprises all residues that are C-terminal to the HA1/HA2 cleavage peptide of the precursor HA0 protein, including the hydrophobic peptide responsible for insertion within the host cell membrane during the process of membrane fusion (see FIGS. 1B and 4).

The term "HA stalk" when used herein refers to the region of the HA protein including residues from approximately 1-42 and 274-330 of the HA1 chain as well as residues (1-174) of the HA2 chain. The stalk is located in the membrane-proximal region of the HA, directly beneath the vestigial esterase domain of the HA1 globular head.

Further Aspects and Embodiments of the Invention

As explained above, in one aspect, the invention relates to a modified influenza haemagglutinin (HA) antigen comprising additional Asn-linked glycosylation on at least two surface patches selected from the group of surfaces patches consisting of: Site A, Site B, Site C, Site, D and Site E.

Site A is defined as the surface patch consisting of the surface residues in the mature protein of HA from the virus A/Vietnam/1203/04, as set forth in List A, or the surface residues corresponding to those in List A in the mature protein of HA from a different influenza virus.

List A:
Q115, P118, K119, S120, S121, H125, E126, A127, S128, L129, V131, S133, A134, P136, Y137, Q138, G139, K140, S141, S142, R145, N146, V148, R162 and Y164.

Site B is defined as the surface patch consisting of the surface residues in the mature protein of HA from the virus A/Vietnam/1203/04, as set forth in List B, or the surface residues corresponding to those in List B in the mature protein of HA from a different influenza virus.

List B:
S123, S124, I151, K152, K153, N154, S155, T156, T159, K161, N182, D183, A184, A185, E186, T187, K188, L189, Q192, N193 and P194.

Site C is defined as the surface patch consisting of the surface residues in the mature protein of HA from the virus A/Vietnam/1203/04, as set forth in List C, or the surface residues corresponding to those in List C in the mature protein of HA from a different influenza virus.

List C:
E34, K35, K36, H37, N38, K40, L41, C42, D43, L44, E270, G272, N273, N275, T276, K277, F291, I294, P296, L297, E301, C302, K304, Y305, V306, K307, S308, N309 and R310

Site D is defined as the surface patch consisting of the surface residues in the mature protein of HA from the virus A/Vietnam/1203/04, as set forth in List D, or the surface residues corresponding to those in List D in the mature protein of HA from a different influenza virus.

List D:
L89, F95, N96, E112, I114, S163, N165, N166, T167, N168, Q169, E170, D171, L172, L175, I178, Y197, S199, S203, T204, L205, R208, L209, V210, P211, R212, I213, A214, T215, Q222, S223, G224, R225, M226, K234, N236, A238, N240, E242, S243, N244

Site E is defined as the surface patch consisting of the surface residues in the mature protein of HA from the virus A/Vietnam/1203/04, as set forth in List E, or the surface residues corresponding to those in List E in the mature protein of HA from a different influenza virus.

List E:
K48, L50, R53, D54, A58, M66, E69, I71, N72, V73, P74, E75, Y78, I79, V80, A83, N84, V86, K102, H110, V257, K258, K259 and S262

In one embodiment, the HA antigen comprises additional Asn-linked glycosylation attached to:
i) one or more amino acid residues of Site A, and
ii) one or more amino acid residues of Site B,
optionally further comprising additional Asn-linked glycosylation attached to one or more amino acid residues of Site D.

In another embodiment, the HA antigen comprises additional Asn-linked glycosylation attached to:
i) one or more amino acid residues of Site C,
ii) one or more amino acid residues of Site D, and
iii) one or more amino acid residues of Site E,
optionally further comprising additional Asn-linked glycosylation attached to one or more amino acid residues of Site A.

In a further embodiment, the HA antigen comprises additional Asn-linked glycosylation attached to:
i) one or more amino acid residues of Site A,
ii) one or more amino acid residues of Site B, and
iii) one or more amino acid residues of Site E,
optionally further comprising additional Asn-linked glycosylation attached to:
i) one or more amino acid residues of Site C, and
ii) one or more amino acid residues of Site D.

In a further embodiment, the HA antigen described herein further comprises additional Asn-linked glycosylation attached to one or more amino acid residues of Site A, Site B, Site C, Site D or Site E, or any combination thereof.

In a specific embodiment, a Lys to Asn substitution has been made at position 140 of SEQ ID NO:1, or a variant of SEQ ID NO:1 has been modified to introduce to an acceptor site for Asn-linked glycosylation at position 140 or a position corresponding to 140.

In another embodiment, a Glu to Asn substitution has been made at position 126 of SEQ ID NO:1, or a variant of SEQ ID NO:1 has been modified to introduce to an acceptor site for Asn-linked glycosylation at position 126 or a position corresponding to 126.

In a further embodiment, a Lys to Asn substitution has been made at position 119 of SEQ ID NO:1, or a variant of SEQ ID NO:1 has been modified to introduce to an acceptor site for Asn-linked glycosylation at position 119 or a position corresponding to 119.

In a further embodiment, a Ser to Asn substitution has been made at position 121 of SEQ ID NO:1, or a variant of SEQ ID NO:1 has been modified to introduce to an acceptor site for Asn-linked glycosylation at position 121 or a position corresponding to 121.

In a further embodiment, a Gln to Asn substitution has been made at position 192 of SEQ ID NO:1 and an Pro to Thr or Pro to Ser substitution has been made at position 194 of SEQ ID NO:1, or corresponding residues in a variant of SEQ ID NO:1 have been substituted to introduce to an acceptor site for Asn-linked glycosylation at position 192.

In a further embodiment, a Pro to Asn substitution has been made at position 194 of SEQ ID NO:1, or a variant of SEQ ID NO:1 has been modified to introduce to an acceptor site for Asn-linked glycosylation at position 194 or a position corresponding to 194.

In a further embodiment, a Lys to Asn substitution has been made at position 307 of SEQ ID NO:1 and an Asn to Thr or Asn to Ser substitution has been made at position 309 of SEQ ID NO:1, or corresponding residues in a variant of SEQ ID NO:1 have been substituted to introduce to an acceptor site for Asn-linked glycosylation at position 307.

In a further embodiment, a Glu to Ser or Glu to Thr substitution has been made at position 242 of SEQ ID NO:1, or a variant of SEQ ID NO:1 has been modified to introduce to an acceptor site for Asn-linked glycosylation at position 240 or a position corresponding to 240.

In a further embodiment, a Pro to Ser or Pro to Thr substitution has been made at position 74 of SEQ ID NO:1, or a variant of SEQ ID NO:1 has been modified to introduce to an acceptor site for Asn-linked glycosylation at position 72 or a position corresponding to 72.

In a specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Glu to Asn substitution has been made at position 126 of SEQ ID NO:1, or a variant of SEQ ID NO:1 has been modified to introduce to an acceptor site for Asn-linked glycosylation at position 126 or a position corresponding to 126, and
a Pro to Asn substitution has been made at position 194 of SEQ ID NO:1, or a variant of SEQ ID NO:1 has been modified to introduce to an acceptor site for Asn-linked glycosylation at position 194 or a position corresponding to 194.

In a further specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Glu to Asn substitution has been made at position 126 of SEQ ID NO:1, or a variant of SEQ ID NO:1 has been modified to introduce to an acceptor site for Asn-linked glycosylation at position 126 or a position corresponding to 126, and
a Pro to Asn substitution has been made at position 194 of SEQ ID NO:1, or a variant of SEQ ID NO:1 has been modified to introduce to an acceptor site for Asn-linked glycosylation at position 194 or a position corresponding to 194, and
a Pro to Ser or Pro to Thr substitution has been made at position 74 of SEQ ID NO:1, or a variant of SEQ ID NO:1 has been modified to introduce to an acceptor site for Asn-linked glycosylation at position 72 or a position corresponding to 72.

In a further specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Glu to Asn substitution has been made at position 126 of SEQ ID NO:1, or a variant of SEQ ID NO:1 has been modified to introduce to an acceptor site for Asn-linked glycosylation at position 126 or a position corresponding to 126, and
a Pro to Asn substitution has been made at position 194 of SEQ ID NO:1, or a variant of SEQ ID NO:1 has been modified to introduce to an acceptor site for Asn-linked glycosylation at position 194 or a position corresponding to 194, and
a Lys to Asn substitution has been made at position 307 of SEQ ID NO:1 and an Asn to Thr or Asn to Ser substitution has been made at position 309 of SEQ ID NO:1, or corresponding residues in a variant of SEQ ID NO:1 have been substituted to introduce to an acceptor site for Asn-linked glycosylation at position 307.

In a further specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Lys to Asn substitution has been made at position 119 of SEQ ID NO:1, or a variant of SEQ ID NO:1 has been modified to introduce to an acceptor site for Asn-linked glycosylation at position 119 or a position corresponding to 119, and
a Lys to Asn substitution has been made at position 307 of SEQ ID NO:1 and an Asn to Thr or Asn to Ser substitution has been made at position 309 of SEQ ID NO:1, or corresponding residues in a variant of SEQ ID NO:1 have been substituted to introduce to an acceptor site for Asn-linked glycosylation at position 307, and
a Pro to Ser or Pro to Thr substitution has been made at position 74 of SEQ ID NO:1, or a variant of SEQ ID NO:1 has been modified to introduce to an acceptor site for Asn-linked glycosylation at position 72 or a position corresponding to 72.

In a further specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Ser to Asn substitution has been made at position 121 of SEQ ID NO:1, or a variant of SEQ ID NO:1 has been modified to introduce to an acceptor site for Asn-linked glycosylation at position 121 or a position corresponding to 121, and
a Lys to Asn substitution has been made at position 307 of SEQ ID NO:1 and an Asn to Thr or Asn to Ser substitution has been made at position 309 of SEQ ID NO:1, or corresponding residues in a variant of SEQ ID NO:1 have been substituted to introduce to an acceptor site for Asn-linked glycosylation at position 307, and
a Pro to Ser or Pro to Thr substitution has been made at position 74 of SEQ ID NO:1, or a variant of SEQ ID NO:1 has been modified to introduce to an acceptor site for Asn-linked glycosylation at position 72 or a position corresponding to 72.

In a further specific embodiment:
a Lys to Asn substitution has been made at position 140 of SEQ ID NO:1, or a variant of SEQ ID NO:1 has been modified to introduce to an acceptor site for Asn-linked glycosylation at position 140 or a position corresponding to 140, and
a Lys to Asn substitution has been made at position 307 of SEQ ID NO:1 and an Asn to Thr or Asn to Ser substitution has been made at position 309 of SEQ ID NO:1, or corresponding residues in a variant of SEQ ID NO:1 have been substituted to introduce to an acceptor site for Asn-linked glycosylation at position 307, and
a Glu to Ser or Glu to Thr substitution has been made at position 242 of SEQ ID NO:1, or a variant of SEQ ID NO:1 has been modified to introduce to an acceptor site for Asn-linked glycosylation at position 240 or a position corresponding to 240, and
a Pro to Ser or Pro to Thr substitution has been made at position 74 of SEQ ID NO:1, or a variant of SEQ ID NO:1 has been modified to introduce to an acceptor site for Asn-linked glycosylation at position 72 or a position corresponding to 72.

The HA antigen may be from any type or subtype (e.g. H1 to H16) of influenza strain. In one embodiment, the HA antigen is from a strain selected from the group consisting of: an H1, an H2, an H3, an H5, an H7 and an H9 strain. Preferably, the HA antigen in from an H5 strain.

In some embodiments, the modified HA has a sequence that, except for the mutations to introduce glycosylation sites, is identical to HA from a pandemic strain. By pandemic strain, it is meant a new influenza virus against which the large majority of the human population has no immunity. Suitable pandemic strains are, for example H5N1, H9N2, H7N7, H2N2, H7N1, H7N3, H10N7, H5N2 and H1N1. Alternatively, the modified HA has a sequence that, except for the mutations to introduce glycosylation sites, is identical to HA from a non-pandemic strain.

The HA antigen may be a full length HA protein or a fragment thereof, for example a truncated variant of HA. In particular, in some embodiments, the HA antigen may lack the HA stalk, or part of the stalk, such as more than 25%, e.g. more than 50%, such as more than 75% of the amino acid residues of the stalk or lack the HA2 part of the stalk.

The HA antigen may also contain further sequences that promote secretion and/or facilitate purification. Such sequences may be removed later, e.g. after purification.

As explained above, in a further aspect, a polynucleotide encoding a modified HA antigen as described herein is provided. Such a polynucleotide can be designed and/or generated on the basis of a naturally-occurring HA, e.g. an HA from an influenza strain isolated from nature. The polynucleotide may thus be modified to introduce sequence the code for acceptor sites for Asn-linked glycosylation, described above. The polynucleotide may be further modified to delete parts of HA, so as to code for an HA fragment. In other embodiment, the polynucleotide may be modified to add nucleotides that code for amino-acid sequences that promote secretion and/or facilitate purification In a further aspect, an immunogenic composition comprising an antigen as defined herein and a pharmaceutically-acceptable carrier is provided.

In one embodiment, said composition further comprises an adjuvant. In one embodiment, the adjuvant is an oil-in-water emulsion adjuvant. Oil in water emulsions, such as MF59 or AS03 are well known in the art, and have been suggested to be useful as adjuvant compositions (EP 399843; WO 95/17210).

In one embodiment, said composition is monovalent, i.e. only comprises one influenza HA. In alternative embodiments, the composition is multivalent, i.e. comprises multiple influenza virus antigens. For example, the composition may be bivalent, trivalent, or quadrivalent.

In a further embodiment, said composition is for use in medicine, such as for use in the prevention of influenza.

In an even further embodiment, said composition is for use in the prevention of influenza caused by a different clade than the clade on which the HA antigen was based, i.e. a different clade from the clade to which the modified HA antigen belongs. For example, a modified clade 1 HA antigen could be used for protection against influenza caused by a non-clade 1 virus, e.g. a clade 2 virus.

In a further aspect, there is provided a method of prevention and/or treatment against influenza disease, comprising the administration of an antigen or immunogenic composition as described herein to a person in need thereof.

In one embodiment of the above described method or use less than 15 micrograms, such as between 3.75 and 10 micrograms of Ha is administered per dose.

In a further aspect, there is provided a method for producing an antigen as defined herein comprising expressing a polynucleotide as defined herein in a eukaryotic cell. In one embodiment, said cell is a mammalian cell, e.g. a CHO cell, or an insect cell.

Populations to Vaccinate

The target population to vaccinate with the immunogenic compositions of the invention is the entire population, e.g. healthy young adults (e.g. aged 18-60), elderly (typically aged above 60) or infants/children. The target population may in particular be immuno-compromised. Immuno-compromised humans generally are less well able to respond to an antigen, in particular to an influenza antigen, in comparison to healthy adults.

In one aspect according to the invention, the target population is a population which is unprimed against influenza, either being naïve (such as vis à vis a pandemic strain), or having failed to respond previously to influenza infection or vaccination. Suitably the target population is elderly persons suitably aged at least 60, or 65 years and over, younger high-risk adults (i.e. between 18 and 60 years of age) such as people working in health institutions, or those young adults with a risk factor such as cardiovascular and pulmonary disease, or diabetes. Another target population is all children 6 months of age and over, who experience a relatively high influenza-related hospitalization rate. In particular, the present invention is suitable for a pediatric use in children between 6 months and 3 years of age, or between 3 years and 8 years of age, such as between 4 years and 8 years of age, or between 9 years and 17 years of age.

The composition of the invention may be administered by any suitable delivery route, such as intradermal, mucosal e.g. intranasal, oral, intramuscular or subcutaneous. Other delivery routes are well known in the art.

The intramuscular delivery route is particularly suitable for the adjuvanted influenza composition.

In one aspect of the present invention, the adjuvanted immunogenic composition for the first administration may be given intramuscularly, and the boosting composition, either adjuvanted or not, may be administered through a different route, for example intradermal, subcutaneous or intranasal.

An aspect of the present invention provides an influenza immunogenic composition for revaccination of humans previously vaccinated with an immunogenic composition of the invention, as well as a method of prevention and/or treatment against influenza disease, wherein a first immunogenic composition of the invention is first administered and a second immunogenic composition comprising an antigen or an antigenic preparation from at least one influenza virus strain is administered.

Typically revaccination is made at least 6 months after the first vaccination(s), suitably 8 to 14 months after, suitably at around 10 to 12 months after.

Vaccination Regimes, Dosing and Efficacy Criteria

Suitably, the immunogenic compositions for use according to the present invention are a standard 0.5 ml injectable dose in most cases, and contain 15 μg or less, of haemagglutinin antigen component from an influenza virus strain, as measured by single radial immunodiffusion (SRD) (J. M. Wood et al.: J. Biol. Stand. 5 (1977) 237-247; J. M. Wood et al., J. Biol. Stand. 9 (1981) 317-330). Suitably the vaccine dose volume will be between 0.25 ml and 1 ml, in particular a standard 0.5 ml, or 0.7 ml vaccine dose volume. Slight adaptation of the dose volume will be made routinely depending on the HA concentration in the original bulk sample and depending also on the delivery route with smaller doses being given by the intranasal or intradermal route. Suitably said immunogenic compositions for use according to the invention contain a low amount of HA antigen—e.g. any of 1, 2, 3, 4, 5, 6, 7, 8, 9, 10, 11, 12, 13, 14 μg of HA per influenza virus strain or which does not exceed 15 μg of HA per strain. Said low amount of HA amount may be as low as practically feasible provided that it allows to formulate a vaccine which meets the international e.g. EU or FDA criteria for efficacy, as detailed below (see Table 1 and the specific parameters as set forth). A suitable low amount of HA is between 1 to 7.5 μg of HA per influenza virus strain, suitably between 3.5 to 5 μg such as 3.75 or 3.8 μg of HA per influenza virus strain, typically about 5 μg of HA per influenza virus strain. Another suitable amount of HA is between 0.1 and 5 μg of HA per influenza virus strain, suitably between 1.0 and 2 μg of HA per influenza virus strain such as 1.9 μg of HA per influenza virus strain.

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). *Note for harmonization of requirements for influenza vaccines*, 1997. CHMP/BWP/214/96 circular No 96-0666:1-22) for clinical trials related to annual licensing procedures of influenza vaccines (Table below).

CHMP Criteria

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre ≥1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of ≥1:40 or who were seropositive prior to vaccination and have a significant 4-fold increase in titre post-vaccination; it is normally accepted as indicating protection.

The requirements are different for adult populations (18-60 years) and elderly populations (>60 years). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best correlate of protection (Beyer et al. (1998) Clin Drug Invest 15:1). The compositions for use according to the present invention suitably meet at least one such criteria for the influenza virus strain included in the composition (one criteria is enough to obtain approval), suitably at least two, or typically at least all three criteria for protection. Suitably the above response(s) is(are) obtained after one dose, or after two doses.

In a yet further aspect, there is provided an anti-HA antibody that competes for binding to haemagglutinin with an antibody comprising a heavy chain comprising the CDR1, CDR2 and CDR3 sequences as set forth in SEQ ID NO: 6, 7 and 8, and a light chain comprising the CDR1, CDR2 and CDR3 sequences as set forth in SEQ ID NO:9, 10 and 11.

In one embodiment, the antibody binds the same epitope as an antibody comprising a heavy chain comprising the CDR1, CDR2 and CDR3 sequences as set forth in SEQ ID NO: 6, 7 and 8, and a light chain comprising the CDR1, CDR2 and CDR3 sequences as set forth in SEQ ID NO:9, 10 and 11.

In a further embodiment, the antibody comprises a heavy chain comprising the CDR1, CDR2 and CDR3 sequences as set forth in SEQ ID NO: 6, 7 and 8, and a light chain comprising the CDR1, CDR2 and CDR3 sequences as set forth in SEQ ID NO:9, 10 and 11.

In a further embodiment, the antibody comprises a heavy chain comprising sequences as set forth in SEQ ID NO:2, and a light chain comprising the sequence as set forth in SEQ ID NO:3.

The antibody may be any type of antibody, including any isotype, e.g. IgG. In one embodiment, the antibody is a human antibody or a humanised antibody.

The invention also relates to the antibody described herein for use in the treatment or prevention of influenza.

The antibodies of the invention may be used in combination with other molecules useful in diagnosis, prophylaxis and/or treatment. They can be used in vitro, ex vivo or in vivo. For example, antibodies may be co-administered with a vaccine against influenza virus or with other anti-viral agents.

Antibodies will typically be formulated for parenteral administration, such as for intravenous, intramuscular or subcutaneous administration. Upon formulation, solutions will be administered in a manner compatible with the dosage formulation or in such amount as is therapeutically effective. Some variation in dosage will often occur depending on the condition of the subject being treated.

The teaching of all references in the present application, including patent applications and granted patents, are herein fully incorporated by reference.

For the avoidance of doubt the terms 'comprising', 'comprise' and 'comprises' herein is intended by the inventors to be optionally substitutable with the terms 'consisting of', 'consist of', and 'consists of', respectively, in every instance.

The invention will be further described by reference to the following, non-limiting, examples:

EXAMPLES

Example 1: Production of Antigen and Antibodies

Viruses and Recombinant Hemagglutinins

Wild-type or reverse genetics-derived A/Vietnam/1203/2004 (H5N1; Viet04), A/Indonesia/05/2005 (H5N1; Indo05), A/BHG/Qinghai/12/2005 (H5N1; Qinghai05), A/Anhui/5/2005 (H5N1; Anhui05), A/chicken/NJ/17169/1993 (H5N2; ckNJ93) and A/Brisbane/59/2007 (H1N1; Bris59) viruses were propagated in embryonated eggs. Inactivation of viruses was carried out by treatment with β-propiolactone (BPL; 0.05%) for 48 hours at 4° C. (Budowsky et al. (1991) Vaccine 9, 398). All experiments using subtype H5N1 highly pathogenic avian influenza viruses were conducted under biosafety level 3 containment facilities including enhancements required by the U.S. Department of Agriculture and Select Agent Program.

Reassortant ckNJ93 and Bris59 viruses containing the internal genes A/Puerto Rico/8/1934 (H1N1; PR8) in combination with HA and NA genes of the donor virus were derived by classical reassortment. HPAI H5N1 viruses from distinct clades, were produced by reverse genetics (RG) methods to combine modified HA genes lacking the multibasic cleavage site, and wild-type NA with the remaining genes from PR8 (O'Neill and Donis (2009) Curr Top Microbiol Immunol 333, 83), yielding RG-A/Vietnam/1203/2004-PR8, RG-A/Indonesia/5/2005-PR8 and RG-A/Anhui/5/2005-PR8. All reassortant viruses were all grown in embryonated eggs, using established viral culture techniques (Hossain et al. (2010) Clin Vaccine Immunol 18).

For production of recombinant hemagglutinins, residues comprising the mature hemagglutinin ectodomains from Viet04 (H5N1, clade 1; group 1), Indo05 (H5N1, clade 2.1; group 1), Anhui05 (H5N1, clade 2.3.4: group 1) A/Egypt/N03072/2010 (H5N1, clade 2.2.1; group 1), A/Hubei/1/2010 (H5N1, clade 2.3.2; group 1), A/Darwin/2001/2009 (H1N1; group 1), A/Brisbane/59/2007 (H1N1; group 1), A/HongKong/2108/2003 (H9N2; group 1), A/Brisbane/10/2007 (H3N2; group 2) and A/New York/107/2003 (H7N2; group 2) were cloned into the baculovirus shuttle vector pAcGP67-A (BD Pharmingen) and expressed as described previously (Stevens et al. (2006, Science 312, 404; Carney et al. Clin Vaccine Immunol 17, 1407; Yang et al. PLoS Curr 2, RRN1152; Yang et al. PLoS Pathog 6, e1001081). Briefly, *Tricoplusia ni* (High 5) cells (Invitrogen) were infected with recombinant Viet04 baculovirus at an MOT of 5-10 at 28° C. for 72 hours. The secreted recombinant HA protein was purified from tissue culture supernatant by metal affinity chromatography and subsequent size exclusion gel filtration chromatography (Superdex 200 16/60 column; GE Healthcare). The C-terminal foldon/histidine tag was removed by thrombin treatment using 3 U enzyme/mg HA overnight at 4° C.

Anti-H5 Monoclonal Antibodies

Anti-H5 HA murine monoclonal antibodies (mAbs) analyzed in this study were derived from different sources. Three mAbs were obtained from Rockland Immunochemicals Inc.: VN04-2, VN04-8 and VN04-10. Five other mAbs (5C5.1.1, 16C8.2.7, 16A8.2.3, 17A2.1.2 and 21G8.6) were all generated by conventional hybridoma technology, through immunization of mice with inactivated H5N1 virus (Vietn04, clade 1) into naïve mice. A further 12 mAbs (as designated in Table 1) were derived from BALB/c mice following immunization with several antigenically divergent H5 viruses; either by infection, or injection of inactivated virus and recombinant HA proteins.

Monoclonal antibodies 1A2, 1E11, 2H8, 3B7 and 4D4 were produced by exposure to a sub-lethal dose (104 median egg infectious doses, EID50) of live RG-A/Indonesia/5/05-PR8 (clade 2.1) virus, followed by two sequential vaccinations with Viet04 (clade 1) monovalent vaccine. Monoclonal Antibodies 5G4, 5G11, 5H6, 6C3, 6G12, 6H10 and 7B8 were produced by inoculation with live RG-A/Vietnam/1203/04-PR8 (clade 1) virus, Qinghai05 (clade 2.2) monovalent vaccine, and a final boost with 10 µg A/Egret/Egypt/1162NAMRU3/2006 recombinant HA (clade 2.2).

Expression and Purification of Monoclonal Antibodies 1A2, 5C5 and 7B8

1A2, 5C5 and 7B8 murine hybridoma cells were cultured in DMEM (Invitrogen) supplemented with 2 mM L-glutamine (Sigma), 50 mg/L sodium pyruvate (Sigma), 1× non-essential amino acids (Invitrogen) and 10% heat-inactivated ultra low IgG fetal bovine serum (Invitrogen), using Celline CL-1000 flasks (BD-Pharmingen). Monoclonal IgG antibodies were purified from tissue culture supernatant by affinity chromatography using a protein A Hi-trap column (GE Healthcare), according to the manufacturer's guidelines.

Example 2: Assays

Microneutralization Assay

Microneutralization assays were performed using Madin-Darby canine kidney (MDCK) obtained from the American Type Culture Collection (ATCC) and maintained in DMEM, supplemented with 10% FBS (Invitrogen), 0.1% penicillin/streptomycin, and 0.1% glutamine. Two-fold serial dilutions of Abs were performed in a 50 µl volume of viral diluent in immunoassay plates as described previously (Rowe et al. (1999) J Clin Microbiol 37, 937).

Hemagglutination Inhibition Assay

Hemagglutination Inhibition (HI) assays were performed with turkey erythrocytes (University of Georgia, Athens, Ga.) using standard methods, as previously described (Hossain et al. (2010) Clin Vaccine Immunol 18). The HI titer was expressed as the reciprocal of the highest dilution of the samples preventing hemagglutination.

Epitope Mapping and Cell-Based ELISA

Figure 1B:
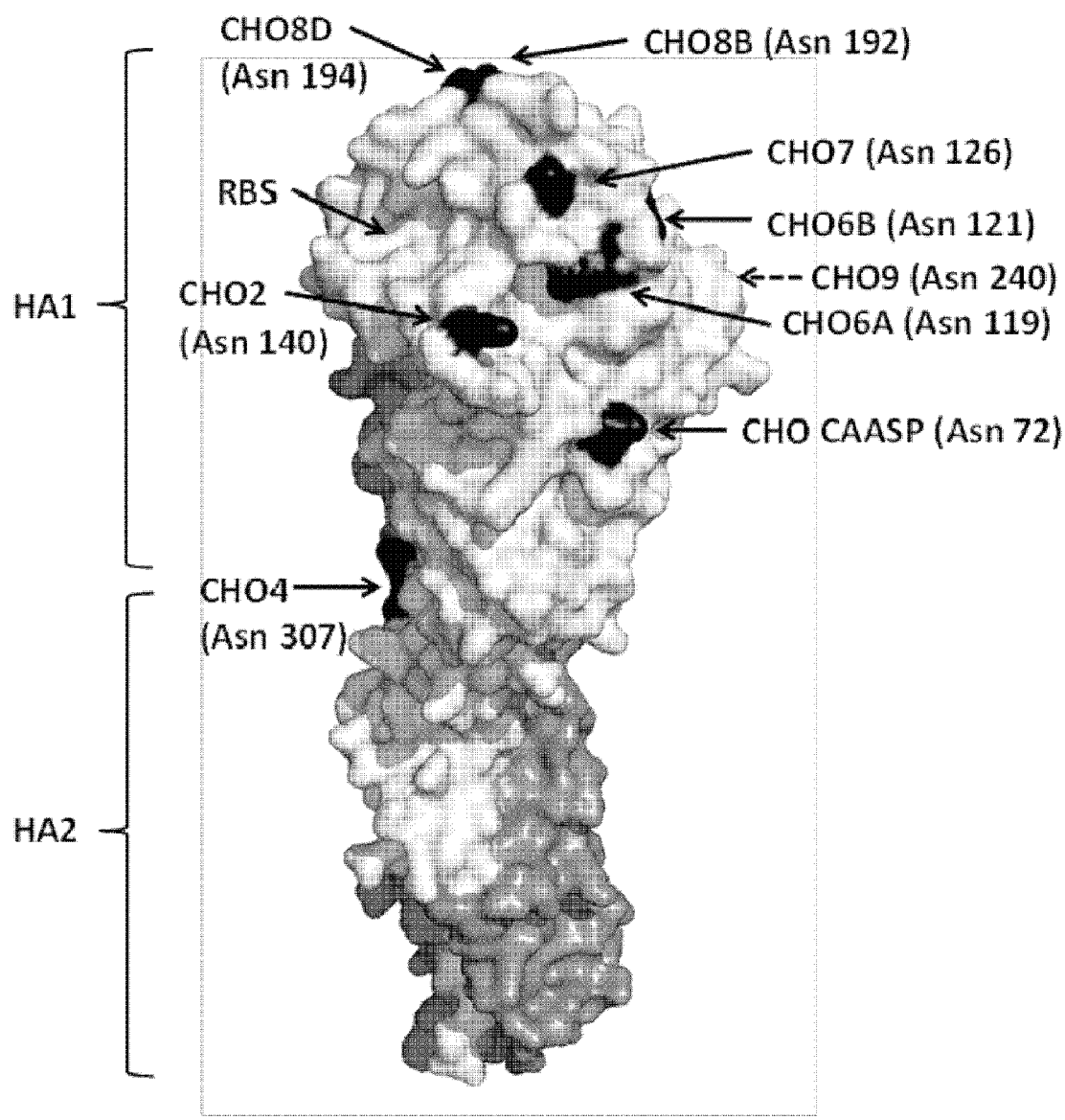

For the expression of soluble H5 HA trimers at the surface of mammalian cells, the full-length HA gene from Viet04 was cloned into the pEF-V5His expression vector. A screen comprising 26 unique point mutations at surface of the HA was designed, including Lys36Glu, His37Glu, Lys40Glu, Lys48Glu, Arg53Glu, Met66Lys, Asn72Asp, Glu75Lys, His110Lys, Gln115Lys, Ser120Tyr, Ile121Thr, Glu126Lys, Ser128Lys, Gln136Glu, Lys140Glu, Lys153Glu, Lys161Glu, Gln169Glu, Asp183Asn, Lys189Glu, Gln192Glu, Glu270Lys, Asn273Asp, Asn275Asp and Lys277Glu Mutations were incorporated using the QuickChange Multi Site-Directed mutagenesis kit (Agilent Technologies) and the presence of mutations was confirmed by sequence analysis. The spatial arrangement of mutants is illustrated in FIG. 1.

For cell-based ELISA, 293T cells were cultured in 96-well plates at a cell density of 1×105/cm3 in DMEM supplemented with 10% FCS (Invitrogen), Non-essential amino acids (Invitrogen), Sodium pyruvate (Invitrogen) and 2 mM L-glutamine (Sigma). Cells grown to ~80% confluency were transfected, using the Lipofectamine-1000 transfection reagent (Invitrogen). Three days post-transfection, cells were fixed with 4% formaldehyde for 15 min at room temperature, then treated with 1% H2O2-methanol for 15 min at room temp and blocked with 3% BSA-PBS for 1 hour at 37° C. Cells were then incubated with monoclonal antibody, at 1 µg/ml in PBS with 1% (w/v) BSA, 0.05% (v/v) Tween 20. ELISA was developed using HRP-conjugated secondary anti-mouse IgGFc. Expression of all mutant and wild-type H5 HA proteins at the surface of 293T cells was confirmed by primary incubation with mouse antiserum raised against Viet04 virus. All measurements were expressed as percentages of binding to the wild type control protein. Surface mutations were grouped into structurally-analogous antigenic sites defined at the surface of H3 HA (A-E) (Wiley et al (1981) Nature 289, 373 and H1 HA (Sa, Sb, Ca and Cb) (Gerhard et al. (1981) Nature 290, 713), respectively, were grouped into 5 regions across the surface of H5 HA, designated antigenic sites A-E (FIG. 1).

Biolayer Interferometry and Binding Assays

An Octet Red instrument (Fortebio, Inc., Menlo Park, Calif.) was used for all binding studies. Data was analyzed using the system software and exported as a Microsoft Excel file for analysis and presentation in other software packages.

Recombinant HA protein was immobilized on anti-His biosensors at 50-100 µg/mL in kinetics buffer (PBS, pH 7.4, 0.01% BSA, and 0.002% Tween 20). For subtype specificity studies, biosensors were probed with mAb at a concentration of 10 µg/ml in each well. For comparing, 1A2 and 5C5 IgG, Fab and Fab2' molecules binding to recombinant Viet04 and Anhui05, 5-7 different concentrations of each mAb were used, with the highest concentration being 21 nM. Baseline and dissociation steps were carried out in 1× kinetics buffer.

Twelve Abs were identified as possessing neutralization activity against more than one H5 clade (Table 1). Seven of these did not exhibit HI activity, indicating that the neutralizing epitopes were outside the Receptor Binding Domain (RBD). A further ten mAbs were also obtained from commercial sources and academic collaborators for analyses and these are also presented in Table 1. All Abs lacking efficient HI activity (<16) displayed neutralization activity (≥64) against at least two divergent viral clades.

TABLE 1

| mAb | Isotype | HI titer (500 µg/ml) | | | Microneutraliztion (100 µg/ml) | | | Antigenic Site | |
|---|---|---|---|---|---|---|---|---|---|
| | | Clade 1 | Clade 2.1 | N. Am | Clade 1 | Clade 2.1 | N. Am | H5 | H1* |
| 6C3[a] | IgG2a | 64 | <16 | <16 | 1024 | <16 | 32 | A | Sa/Sb |
| 1E11[b] | IgG1 | 128 | 128 | 256 | >1024 | >1024 | >1024 | A/B | Sa/Sb |
| 5G11[a] | IgG1 | 128 | <16 | 128 | >1024 | 512 | >1024 | A/B | Sa/Sb |
| 3B7[b] | IgG1 | <16 | 64 | <16 | 512 | >1024 | >1024 | B | Sa/Sb |
| 6G12[a] | IgG2b | 1024 | 64 | 1024 | >1024 | 64 | >1024 | B | Sa/Sb |
| 5G4[a] | IgG2a | <16 | <16 | <16 | 512 | 512 | <16 | C | Cb |
| 2H8[b] | IgG2a | <16 | <16 | <16 | 256 | 256 | 256 | E/C | Cb |
| 6H10[a] | IgG1 | <16 | <16 | <16 | 256 | 256 | <16 | E/C | Ca/Cb |
| 4D4[b] | IgG2a | <16 | <16 | <16 | 256 | 512 | <16 | E | Ca |
| 1A2[b] | IgG2a | <16 | <16 | <16 | 128 | 1024 | 512 | E | Ca |
| 5H6[a] | IgG2a | <16 | <16 | <16 | 512 | >1024 | 512 | E | Ca |
| 7B8[a] | IgG2a | <16 | <16 | <16 | 64 | 64 | 256 | HA2 | HA2 |
| 16A8.2.3 | IgG1 | 64 | <16 | 64 | 256 | <16 | <16 | A | Sa/Sb |
| 17A2.1.2 | IgG2b | 512 | 512 | 512 | 512 | >1024 | 32 | A/B | Sa/Sb |
| 21G8.6 | IgG2a | 256 | 32 | 512 | 256 | <16 | 512 | A/B | Sa/Sb |
| 5C5.1.1 | IgG2a | 512 | 512 | 256 | >1024 | >1024 | >1024 | A/B | Sa/Sb |
| 16C8.2.7 | IgG2a | 512 | <16 | <16 | 512 | <16 | <16 | B | Sa/Sb |
| VN04-2 | IgG2a | 1024 | <16 | 32 | >1024 | <16 | 32 | A | Sa |
| VN04-8 | IgG1 | 256 | <16 | <16 | 1024 | <16 | <16 | A | Sa |
| VN04-10 | IgG2b | 64 | 128 | <16 | 512 | 1024 | <16 | A | Sa |

*The location of mAb epitopes relative to antigenic sites identified in H1 HA is approximated.
[a]mAbs generated from second vaccination experiment: 1st immunization with Viet04 (clade 1); 2nd immunization with A/BHG/Qinghai/12/2005 (clade 2.2); 3rd immunization with A/chicken/NJ/17169/1993 H5N2; final boost with A/egret/Egypt/1162/2006 recombinant HA (clade 2.2).
[b]mAbs generated from first vaccination experiment: 1st immunization with Indo05 (clade 2.1); 2nd immunization with Viet04 (clade 1); final boost with Viet04 (clade 1).

Protease Protection Assay

Protease protection assay for 1A2 and 5C5 was adapted from the methods of Ekiert et al. (2009) Science 324, 246. Briefly, 20 µg HA or Ab Fab-HA complex were mixed with 100 mM sodium acetate (pH 5.0) or Tris-HCL (pH 8.0) at 37° C. for one hour. Following incubation reactions were equilibrated to room temperature and the pH was neutralized by addition of 200 mM Tris, pH 8.5. Trypsin (Sigma) was added to all samples except controls, at a final ratio of 1:50 by mass for both complex and apo-HA samples. Samples were digested overnight at 37° C. and quenched by addition of non-reducing SDS buffer followed by boiling for 3 min. Samples were analyzed by SDS-PAGE.

Example 3: Identification of Cross-Clade Neutralizing Antibodies

A panel of Abs against H5N1 viruses was produced in BALB/c mice by sequential vaccination with a panel of H5 viruses from different clades and lineages (see Example 1).

Antibodies raised in these animals were screened for cross-reactivity and neutralization by ELISA, micro-neutralization (MN) and hemagglutination inhibition (HI) assays (see Example 2) against H5 viruses from clades 1 (A/Vietnam/1203/2004; Viet04) and 2.1 (A/Indonesia/05/2005; Indo05) as well as a distinct North American H5N2 virus (A/chicken/New Jersey/17169/1993).

To better understand the distribution of cross-neutralizing epitopes on H5 HA, a panel of mutant HA proteins incorporating single or multiple changes to surface-exposed residues across HA1 were expressed on 293-T cells and probed for mAb binding by cell-based ELISA (see Example 2) (FIG. 1).

The approximate epitopes of 21 Abs were identified within four distinct regions on H5 HA1, designated binding sites A, B, C, and E (spatially equivalent to the antigenic sites for human seasonal H3N2 viruses (Otwinowski et al. (1997) Methods in Enzymology 276, 307). Fifteen Abs bound within the vicinity of the RBD (binding sites A and B) and exhibited HI reactivity. Of seven Abs which did not inhibit hemagglutination, six bound within the vestigial esterase domain of HA1 (binding sites C and E) and one bound within the HA1/HA2 fusion peptide domain. Notably, the majority (70%) of neutralizing Abs generated by cross-immunization with multiple H5 viruses bound antigenic sites other than A/B (Table 1). By comparison, neutralizing Abs raised by vaccination with a single H5 virus bound only to these sites, suggesting cross-immunization with multiple clades of H5 viruses focuses immune recognition on conserved epitopes outside the rapidly evolving RBD.

Figure 2:
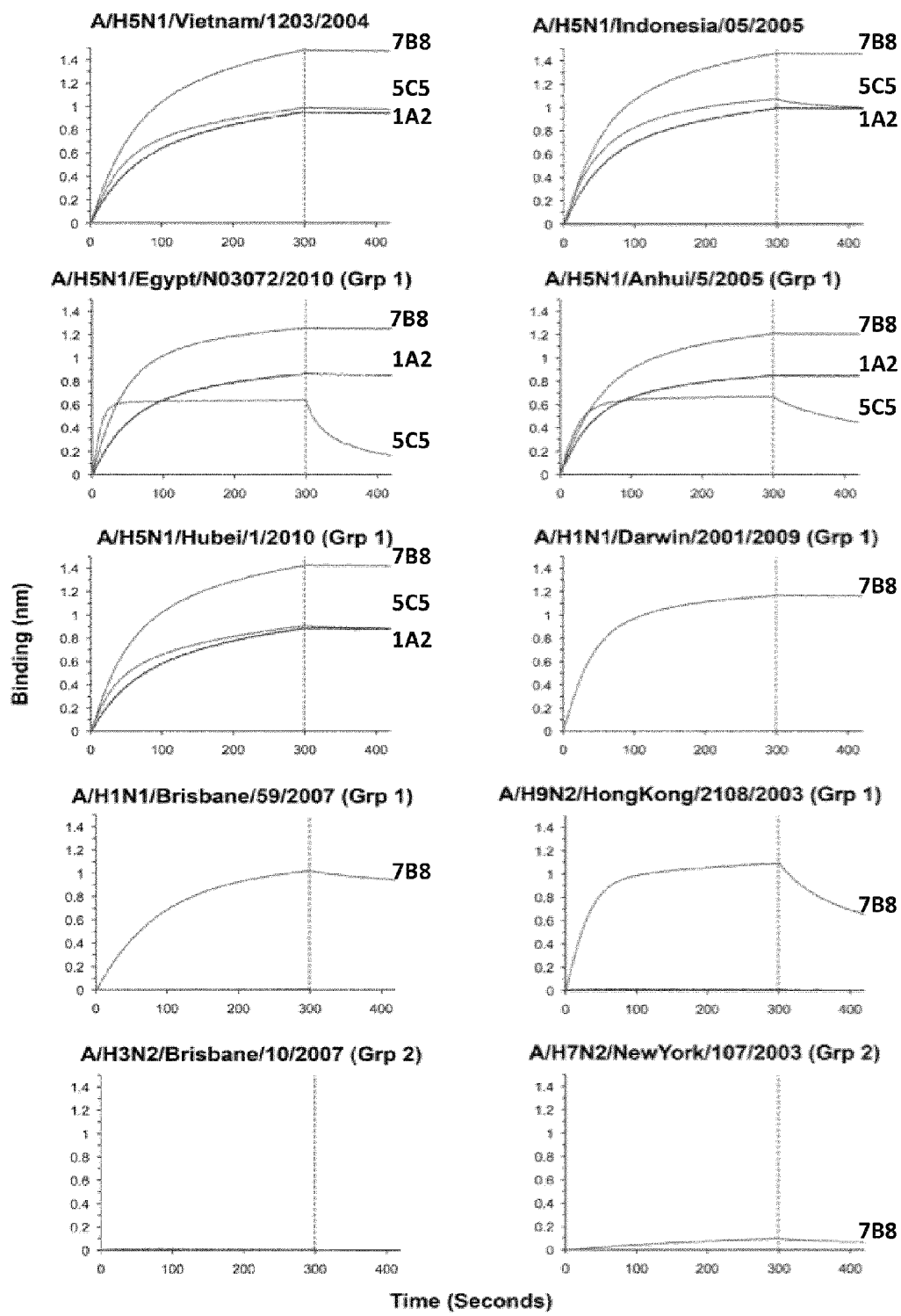
FIG. 2: Kinetic characterization of Abs 1A2, 5C5 and 7B8 interaction with recombinant HA from Viet04 (H5N1, clade 1; group 1), Indo05 (H5N1, clade 2.1; group 1), A/Egypt/N03072/2010 (H5N1, clade 2.2.1; group 1), Anhui05 (H5N1, clade 2.3.4: group 1, A/Hubei/1/2010 (H5N1, clade 2.3.2; group 1), A/Darwin/2001/2009 (H1N1; group 1), A/Brisbane/59/2007 (H1N1; group 1), A/HongKong/2108/2003 (H9N2; group 1), A/Brisbane/10/2007 (H3N2; group 2) and A/New York/107/2003 (H7N2; group 2). Measurements were performed using an Octet Red system (Fortebio Inc.).

To assess the extent of conservation of epitopes at distinct regions of H5 HA we screened Abs against site A/B (5C5), site C/E (1A2) and site HA2 (7B8) for reactivity with a panel of H5 HA selected for vaccine candidates in four distinct clades; 1, 2.1, 2.2.1 and 2.3.4 (FIG. 2). These three Abs bound to all H5 HAs with high affinity, however 5C5 showed reduced reactivity to Anhui05 (clade 2.3.4) and to A/Egypt/N03072/2010 (clade 2.2.1).

7B8 was the only Ab that recognized virus HAs from other group 1 sub-types (H1 and H9) (McCoy et al., (2007) J Appl Crystallogr 40, 658), while group 2 HAs (H3 and H7) were not recognized. Such hetero-subtypic reactivity by 7B8 in the absence of HI activity is indicative of stem-specific cross-protective Abs described previously. These data indicate 7B8 to be an antibody that binds the fusion peptide region of the HA2. Conversely, cross-clade neutralization by 5C5 and 1A2 was specific to H5 viruses (FIG. 2).

Example 4: Assessment of Prophylactic and Therapeutic Efficacy

We next evaluated prophylactic and therapeutic efficacy of 1A2, 5C5 and 7B8 against an otherwise lethal Viet04 virus infection in a BALB/c mouse model.

Eight week-old female Balb/c mice (The Jackson Laboratory, Bar Harbor, Me.) were used in all experiments. For the prophylactic and therapeutic efficacy studies, mice were inoculated by intranasal instillation of 10 MLD50 of Viet04 in a volume of 50 µl of PBS per mouse. Nine groups of five mice received 1A2, 5C5, or 7B8 purified IgG by intraperitoneal injections at either −2 h, +24 h, or +48 h post-infection at a dose of 10 mg kg-1 body weight in 0.5 ml of PBS. One group of mice received an IP injection of 0.5 ml of PBS. Mice were weighed daily and observed for clinical signs of infection for 14 days post-infection. Mice were scored based on clinical signs, including ruffled fur, decreased movement, hunched posture, and neurological disease. Body weight was used as clinical endpoint and mice with body weight loss ≥25% of pre-infection values were euthanized. Animal studies were conducted as per the approved Institutional Animal Care and Use Committee protocols. All experiments using subtype H5N1 highly pathogenic avian influenza viruses were conducted under biosafety level 3 containment animal facilities including enhancements required by the U.S. Department of Agriculture and Select Agent Program.

Figure 3:
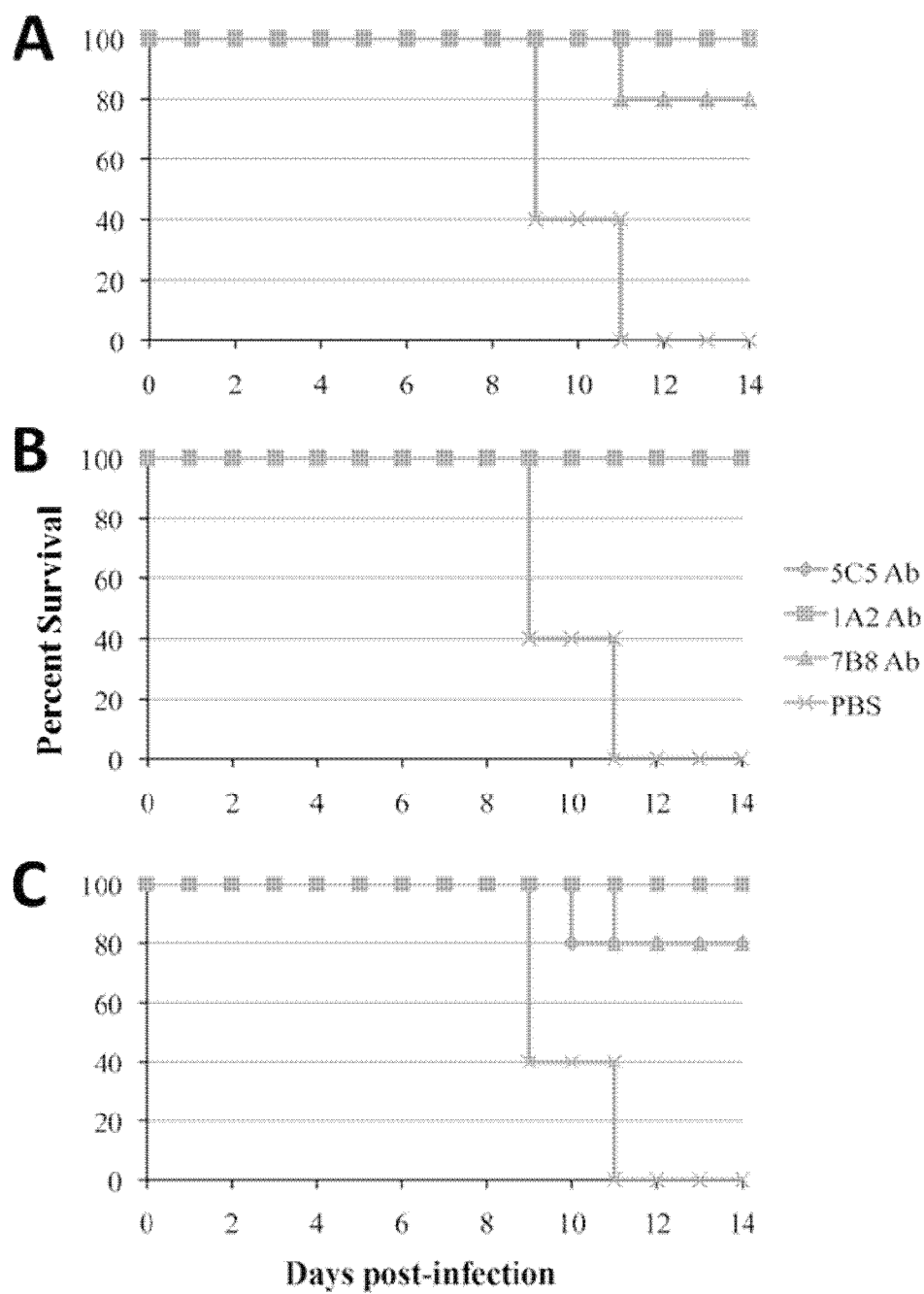
FIG. 3: Prophylactic and therapeutic efficacy of anti-H5 Abs, 1A2, 5C5 and 7B8, in mice against H5N1. A) Prophylactic efficacy as percentage of survival of mice treated with anti-H5 Abs (10 mg/kg), 2 hrs before lethal challenge with 10 LD50 of wild-type A/Vietnam/1203/2004 (Viet04). B) and C) Therapeutic efficacy in mice injected Abs at 24 hrs or 48 hrs after infection, respectively; antibody dose and virus challenge were identical in all three experiments. The curves for 5C5 overlap with those for 1A2 in panels A and B (100% survival). In panel C, the curve for 5C5 overlaps with that of 1A2 until day 9 (100%). From day 11 onwards, it overlaps with that of 7B8 (80%).

All three Abs provided both prophylactic (FIG. 3A) as well as therapeutic protection (80-100% survival) (FIG. 3B/C), with all surviving mice showing no clinical signs for 14 days post-inoculation, whereas all untreated mice reached the termination endpoint by day 11. Both antibodies 5C5 and 1A2, provided complete protection, whilst 7B8 provided partial protection (80% in groups treated 2 before and 48 hr after inoculation), with an increased proportion of animals showing clinical signs of disease (data not shown). These data, coupled with our in vitro MN data, indicated the protective efficacy of Abs correlated positively with the distance of Ab epitopes from the viral membrane, such that Abs that bound to highly exposed epitopes at the top of HA provided the most effective protection.

TABLE 2

Clinical signs of disease for protective efficacy study of 1A2, 5C5, 7B8 nAbs against challenge with wild type Viet04 virus.

| nAb | Time Point | Ruffled Fur | Decreased Mobility | Hunched Posture | Neurological Disease |
|---|---|---|---|---|---|
| 5C5 | 2 hr | 0/5 | 0/5 | 0/5 | 0/5 |
|  | 24 hr | 0/5 | 0/5 | 0/5 | 0/5 |
|  | 48 hr | 5/5 | 1/5 | 1/5 | 0/5 |
| 1A2 | 2 hr | 0/5 | 0/5 | 0/5 | 0/5 |
|  | 24 hr | 0/5 | 0/5 | 0/5 | 0/5 |
|  | 48 hr | 0/5 | 0/5 | 0/5 | 0/5 |

TABLE 2-continued

Clinical signs of disease for protective efficacy study of 1A2, 5C5, 7B8 nAbs against challenge with wild type Viet04 virus.

| nAb | Time Point | Ruffled Fur | Decreased Mobility | Hunched Posture | Neurological Disease |
|---|---|---|---|---|---|
| 7B8 | 2 hr | 1/5 | 0/5 | 1/5 | 0/5 |
|  | 24 hr | 1/5 | 0/5 | 0/5 | 0/5 |
|  | 48 hr | 5/5 | 1/5 | 1/5 | 0/5 |
| PBS | All | 5/5 | 5/5 | 5/5 | 0/5 |

Example 5: Sequencing of IgG H and L Chains

The amino-acid sequence of the 1A2 and 7B8 immunoglobulin heavy (H) and light (L) variable and constant (C1) domains was determined by reverse-transcriptase PCR of mRNA extracted from the 1A2 hybridoma cells. Commercially-available primers, designed for amplification of variable murine IgG heavy and light genes (Novagen), were used to amplify purified mRNA and the amino acid sequence of each gene was determined by sequencing of the resulting cDNA.

Example 6: Analysis of Conservation Amongst HA Subtypes

Protein sequence alignments were generated from the GISAID EpiFlu™ database for all H5 (1997-2011), seasonal H1 (2000-2011) and H3 (2000-2011) hemagglutinin HA1 sequences. Conservation at each position of the HA1 was calculated using the Bioedit Sequence alignment editor {Hall, 1999 #114}. Results were processed in Microsoft Excel and a conservation score >99% was considered as a conserved position. Conservation amongst surface residues was illustrated by coloring molecular surface representations of H5, H1 and H3 HAs, respectively. Molecular models were generated in Swiss Model (Arnold et al. (2006) Bioinformatics 22, 195), and figures were rendered using PYMOL (Delano (2002)).

Example 7: Crystallization Studies

To accurately define the 5C5 and 1A2 epitopes, we determined the crystal structures of both 5C5 and 1A2 Fabs in complex with Viet04 H5 HA.

Preparation of Fab and Fab2'

Purified IgG was digested to Fab and Fc fragments by exposure to 40 µg activated papain protease (Sigma)/mg IgG, in a solution containing 10 mM cysteine, 100 mM sodium acetate pH 5.5, 125 µM EDTA for 2-4 hrs at 37° C. Fab2' was produced by digestion with pepsin protease (Sigma) for 2-4 hrs at 37° C. Fab and Fab2' fragments were subsequently purified from Fc by affinity chromatography using a protein A Hi-trap column (GE Healthcare) and purified to homogeneity by size exclusion gel filtration chromatography (Superdex 75 10/30; GE Healthcare).

Formation and Purification of the 5C5 Fab/HA and 1A2 Fab/HA Complexes

Fab 5C5 and Fab 1A2 were mixed with purified, his-tag depleted, recombinant Viet04 HA trimers at a molar ratio of 5 parts Fab to 1 part HA, to ensure saturation with Fab. The resulting 5C5 Fab-Viet04 HA (5C5/HA) and 1A2 Fab-Viet04 (1A2/HA) complexes were purified away from unbound substrates by size exclusion gel filtration chromatography (Superdex 200 10/30 column; GE Healthcare) in a buffer comprising 50 mM Tris-HCL (pH 8.0), 150 mM NaCl. 5C5/HA and 1A2 HA eluted as single peaks between the 158 kDa and 670 kDa molecular weight markers and was concentrated to 15 mg/ml.

Crystallization and Structure Determination of the 5C5/HA Complex

Initial sparse-matrix crystallization screening was carried out using a Topaz™ Free Interface Diffusion (FID) Crystallizer system (Fluidigm Corporation, San Francisco, Calif.). Hits were obtained after 24 hours in several conditions containing the precipitant PEG 4,000. Following optimization, diffraction quality crystals were obtained at 23° C., using the vapor batch diffusion method under an oil layer (comprising 6 parts paraffin oil/4 parts silicon oil) in 1.0 µl drops containing 5C5/HA in 9% PEG 4,000, 300 mM ammonium tartrate, 5 mM NaCl, 25 mM Tris (pH 8.0). The 5C5 Fab-HA complex dataset was collected from a single crystal to 3.36 Å resolution at the Advanced Photon Source (APS) SER CAT 22-ID beamline. 5C5 Fab-HA crystallized in cubic space group I213. Data collection and refinement statistics are presented in Table 3.

Biol 281, 301) as a search model. A subsequent search using the constant (Fc) domains of a mouse IgG2a Fab (PDB: 3F09 (Zhu et al., (2009) J Am Chem Soc 131, 18206) located the Fc region.

Rigid-body and restrained refinement of the molecular replacement solution was carried out using REFMAC5 (Murshudov et al. (1997) Acta Crystallogr D Biol Crystallogr 53, 240) and model building was performed in Coot (Emsley, Acta Crystallogr D Biol Crystallogr 66, 486). 2Fo-Fc electron density was well defined throughout the model. Notably, residues 79-85 of HA1 adopted a different conformation to those in the apo-H5 HA structure. Additional positive electron density was observed in the region of 3 potential N-linked glycosylation sites. Nine sugar residues were manually fitted into this density at these positions. Restrained refinement of the structure was completed in REFMAC5.

Crystallization and Structure Determination of the 1A2 Fab-H5 Complex

A single crystal of the 1A2/HA complex formed over a period of 5 weeks in a sitting drop containing 15 mg/ml

TABLE 3

Crystallographic data collection and refinement statistics for the 5C5/H5 and 1A2/H5 crystal structures.

|  | 1A2/H5 HA Complex | 5C5/H5 HA Complex |
| --- | --- | --- |
| A. Data processing | | |
| Space Group | R 32 | I $2_1$3 |
| Cell Dimensions | a = b = 141.2 Å, c = 401.2 Å | a = b = c = 219.88 Å |
|  | ($\alpha = \beta = 90°, \gamma = 120°$) | ($\alpha = \beta = \gamma, 90°$) |
| Resolution range (Å) | 50.00-2.60 (2.64-2.60) | 50.00-3.36 (3.42-3.36) |
| Completeness (%) | 99.5 (99.5) | 98.5 (99.6) |
| Redundancy | 3.1 (3.1) | 4.1 (4) |
| $R_{sym}^a$ or $R_{merge}$ (%) | 6.7 (61.6) | 13.4 (74.6) |
| I/σ (I) | 22.4 (1.8) | 10.6 (1.7) |
| B. Refinement | | |
| Reflections (total) | 45,261 (3,330) | 23,670 (1,767) |
| Reflections (test) | 2,412 | 1,277 |
| $R_{cryst}^b/R_{free}^c$ (%) | 22.6/26.1 | 23.0/27.0 |
| Residues/protein atoms | 1,064/7,484 | 912/7,269 |
| Coordinate error[e] (Å) | 0.25 | 0.42 |
| rmsd - bond lengths (Å) | 0.006 | 0.008 |
| rmsd - bond angle (°) | 0.9 | 1.2 |
| Wilson B-value (Å$^2$) | 66.7 | 74.9 |
| Average B value (Å$^2$) | 81.67 | 74.72 |
| Waters | 135 | 0 |
| Carbohydrates atoms | 116 | 115 |
| Ramachandran statistics | | |
| Most favored (%) | 95.4 | 94.2 |
| Allowed (%) | 99.9 | 100 |
| Disallowed (%) | 0.1 | 0 |

[a] Values in parentheses are for the highest resolution shell.
[b] $R_{sym} = 100\Sigma_h\Sigma_i|I_i(h) - <I(h)>|/\Sigma_h I$ (h), where $I_i(h)$ is the ith measurement of the h reflection and $<I(h)>$ is the average value of the reflection intensity.
[c] $R_{cryst} = \Sigma|F_o| - |F_c|/\Sigma|F_o|$, where $F_o$ and $F_c$ are the structure factor amplitudes for the experimental data and from the calculated model, respectively.
[d] $R_{free}$ is $R_{cryst}$ with 5% of the test set structure factors.
[e] Values are based on maximum likelihood Data were processed and scaled using HKL2000 and Denzo (Otwinowski et al. (1997) Methods in Enzymology 276, 307). The 5C5 Fab-HA complex structure was determined by the molecular replacement method using Phaser (McCoy et al. (2007) J Appl Crystallogr 40, 658). A strong solution was obtained for the HA component of the complex using a single monomer of Viet04 HA (chains A and B of PDB: 2FK0 (Stevens et al. (2006) Science 312, 404). An initial search for 5C5 Fab determined the position of the variable (Fv) domains using the Fv component of a mouse IgG1 Fab (PDB: 1WEJ (Mylvaganam et al. (1998) J Mol 1A2/HA in 100 mM ammonium acetate, 50 mM sodium citrate pH 5.6, 15% 2-methy-2-4-pentene-diol (MPD), 5 mM NaCl, 25 mM Tris pH 8.0 at 23° C. After optimizing by streak-seeding of this xtal into drops containing increasing concentrations of MPD, diffraction quality crystals with rhombohedral morphology were produced by streak-seeding into 1 µl volume sitting drops containing 15 mg/ml 1A2/HA in 100 mM ammonium acetate, 50 mM sodium citrate pH 5.6, 18% MPD, 5 mM NaCl, 25 mM Tris-HCl, pH 8.0 at 23° C. The 1A2/HA complex dataset was collected from a single crystal to 2.6 Å resolution at the Advanced Photon Source (APS) SER CAT 22-ID beamline. 1A2 Fab-HA crystallized in rhombohedral space group R32. Data collection and refinement statistics are presented in Table 1.

Data were processed and scaled using HKL2000 and Denzo and the 1A2/HA complex structure was determined by the molecular replacement method using a single monomer of Viet04 HA (chains A and B of PDB: 2FK0) and an IgG2 Fab (PDB: 3DGG (Nettleship et al. (2008) Protein Expr Purif 62, 83) as search models. Subsequent rounds of rigid body refinement using REFMAC5 identified loop regions in the MR search model (several loops below the vestigial esterase domain of HA1 as well as a single loop in the B strand of HA2) that adopted a different orientation in the 2Fo-Fc electron density map. Subsequent Molecular replacement using the Viet04 HA from an antibody complex structure (chains A and B from PDB: 3GBN (Ekiert et al. (2009) Science 324, 246)), in which these loops adopt an alternate conformation to that in 2FK0, identified a solution that refined to show well-defined 2Fo-Fc electron density throughout the HA and 1A2 Fv components of the model and clearly resolved interacting elements within the 1A2 combing site. Molecular replacement of the 1A2 Fc domains using the Fc component of PDB: 3BBG provided a solution that packed and showed clearly-defined 2Fo-Fc electron density throughout the majority of the Fc heavy chain and part of the Fc light chain, with breaks in the density surrounding regions in the C, D, E, F and G strands. Subsequent rounds of rigid-body and restrained refinement in REFMAC failed to improve the quality of electron density in the 1A2 constant domains. Both heavy and light chains exhibited reduced definition in the quality of 2Fo-Fc electron density as well as increased B values throughout the carboxyl-terminal domains of the Fab, indicative of substantial disorder in this region of the complex. The structure of the H5 HA was essentially the same as that of the apo-H5 HA used as a search model. Restrained TLS refinement was carried out using REFMAC5 and model building was carried out using Coot. An additional four carbohydrate moieties, 135 water molecules and 2 MPD molecules were built into the model using Coot.

Validation and Analyses of Structural Data

Residues were numbered in the H5 HA of both complexes according to the mature H5 HA. Residues in the 1A2 and 5C5 Fabs were numbered according to the Kabbat and Wu numbering system. Structural validation was carried out using Molprobity (Davis et al. (2007) Nucleic Acids Res 35, W375) and Procheck as well as the RCSB PDB validation server. The connectivity and nomenclature of carbohydrate moieties was validated using PDBCARE (Glycosciences.de). Model manipulations, RMSD calculations and distance measurements were carried out using Coot and Pymol (Delano 2002). Solvent accessible surface area calculations were carried out using PISA (Krissinel (2007) J Mol Biol 372, 774) and Protorp (Reynolds et al. (2009) Bioinformatics 25, 413). Images were rendered using Pymol.

Example 8: Analysis of the 5C5 Fab-HA and 1A2 Fab-HA Complex Crystal Structures

Figure 5:
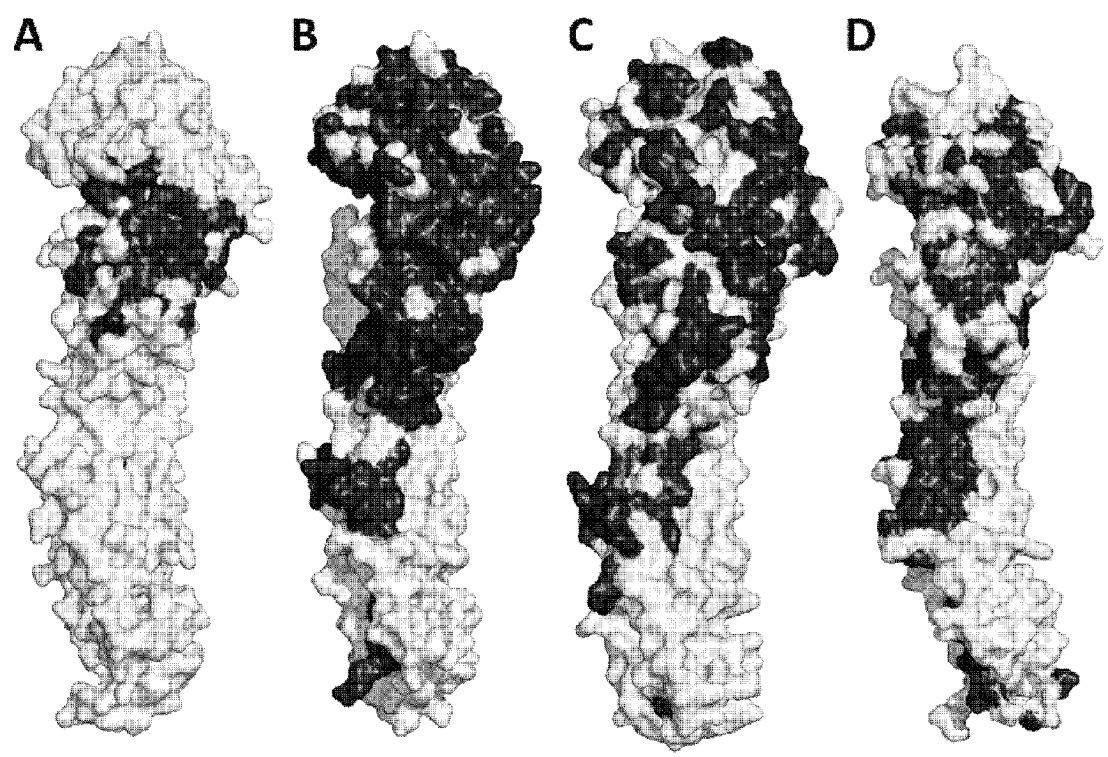
FIG. 5: Conservation in the HA1 amongst residues in viruses identified 1997-2011. A) Molecular surface of Viet04 H5 HA, depicting % conservation amongst H5 HA1 1997-2011; residues conserved >99% are colored black and residues conserved <99%, as well as HA2 are colored grey. B) Equivalent representation are also shown for seasonal (pre-2009) H1, C) contemporary H1 (2000-2009) and D) H3 (2000-2011) subtypes.

Both the 5C5/HA and 1A2/HA complex structures comprise three Fabs bound to a single HA trimer (FIG. 4), with both antibody epitopes located within the globular HA1 domain, albeit at distinct locations (FIG. 5). $2F_o$-$F_c$ electron density is well-defined throughout the HA component of both structures, comprising residues 1-321 (HA1)/4-175 (HA2) and 1-321 (HA1)/1-176 (HA2) of the mature H5 HA ectodomain in the 5C5 Fab-HA and 1A2 Fab-H5 complexes, respectively. The antibody combining sites and Fab variable domains are well-defined in the $2F_o$-$F_c$ electron density maps of both complexes, however the constant domains of 1A2 Fab are partially disordered and exhibit poorly-defined electron density, as observed in other Fab complex structures (Ekiert et al., 2009 Science 324, 246). The H5 HA ectodomain components of both complexes are highly similar to the structure of the un-complexed H5 HA (Stevens et al. (2006) Science 312, 404) and Ab interaction does not produce large changes in the structure of the HA1/HA2 form of the monomer, nor does it affect the association of monomers within the ectodomain trimer.

The relatively modest resolution of the 5C5 Fab-HA complex structure (3.36 Å) prevents the detailed analysis of molecular interactions within the interface, however the overall features of the 5C5 combining site are well defined within the $2F_o$-$F_c$ electron density map and the model may be interpreted with confidence in light of the high-resolution structures used for molecular replacement of H5 HA and 5C5 Fab. The footprint on H5 HA buried by the 5C5 interaction comprises 29 residues, including components of all three highly conserved features of HA RBDs, the 190 helix (Ala185-Glu187), the 130 loop (Gly130-Ser133) and the 220 loop (Lys218-Ser223). The interface also includes residues structurally-equivalent to antigenic sites A and B of H3N2 viruses that border the sialic acid binding site, including Glu126, Ser128 and Lys140 (Antigenic site A), as well as Lys152 and Lys189 (Antigenic site B). Superimposition of a sialic acid moiety bound within the H5 receptor-binding site demonstrates the complete occlusion of the binding site by 5C5 interaction (FIG. 4B). The 5C5 interface buries a solvent accessible surface area of approximately 1,686 Å$^2$ (861 Å$^2$ on 5C5 and 825 Å$^2$ on H5), with both the immunoglobulin variable-heavy chain (VH) and variable light chain (VL) contributing approximately 50% of the area buried upon interaction. In this regard, the interface can be divided into two equal parts, mediated by contacts with the VH and VL, respectively, with VH contacting residues in the sialic acid binding pocket and VL contacting residues within antigenic site A, as well as the 130 loop (FIG. 4B).

Interactions involving 5C5 VH are dominated by complementarity-determining region (CDR) H3, which forms extensive contacts with residues in the conserved sialic acid binding cleft. The side chain of AlaH98 hydrogen bonds with Gln222 and the side chains of TyrH99 and TyrH100a extend towards the floor of the sialic acid binding cavity, contacting Trp149 and hydrogen bonding with Tyr91, as well as Glu186. Tyr91 also extends towards the binding site cavity, hydrogen bonding to Asp183 and Glu186. Contacts with ThrH30-TyrH32 in CDR H1 loop and GluH53 in CDR H3 loop form the boundary of the interface, mediated by hydrogen bonding between the extended side chain of Viet04 Lys218 with SerH32 and GluH53.

The interface formed with VL is dominated by contacts in CDR L2, which forms extensive interactions with residues in the 130-loop. Hydrogen bonding between ThrL52, AsnL53 and LeuL54, at the boundary of the epitope, with Lys152, Asn154 and Ser155, as well as TyrL49 with Lys189 account for the majority of the buried surface area, whilst additional contacts are formed between TrpL92 and GlyL93 in CDRL3 with Lys140 and Ser141. The side chains of Glu126 and Leu129 insert into the shallow cavity formed by the VH/VL interface, bordered by HisL32 and TyrH100a. The 5C5 epitope contains four residues (Lys152-Ser155) within the Sa-equivalent, five residues (Asp183-Glu186, Lys189-Leu190) within the Sb-equivalent and three residues (Lys140, Ser141 and Gly221) within the Ca-equivalent sites of seasonal H1 viruses (see FIG. 6).

The footprint of the 1A2 epitope on the HA is depicted in FIG. 4d and includes 30 residues, comprising all three residues located in antigenic site D and 4 of the 6 residues in antigenic site E of our mutagenesis screen (see FIG. 1, Table 4).

| Antigenic site | Mutants | 1A2 | 5C5.1.1 |
|---|---|---|---|
|  | Wt HA | 100 | 100 |
| site A | ★ Q115K | 101 | 100 |
|  | S120Y | 103 | 108 |
|  | ☆ E126K | 94 | 89 |
|  | ☆ E126K, S128K | 104 | 105 |
|  | ☆ Q136E, K140E | 102 | 97 |
| site B | ☆ K153E, Q192E | 107 | 94 |
|  | ☆ K189E | 116 | 44 |
|  | ☆ K161E, D183N | 103 | 118 |
|  | K161E | 107 | 117 |
|  | ☆ D183N | 111 | 113 |
| site A/B | ☆ K140E, K189E | 113 | 2 |
| site A/D | ★ I114T, Q115K | 86 | 102 |
| site A/E | Q138E, M66K | 105 | 102 |
| site D/E | Q169E, K259E | 94 | 99 |
| site E | ★ K48E | 81 | 104 |
|  | ★ R53E | 116 | 105 |
|  | M66K | 119 | 104 |
|  | R53E, M66K | 117 | 88 |
|  | ★ N72D | 67 | 107 |
|  | ★ E75K | 107 | 97 |
|  | K259E | 112 | 102 |
| site C | K36E | 102 | 97 |
|  | H37E | 97 | 101 |
|  | ★ K40E | 98 | 102 |
|  | E270K | 104 | 107 |
|  | ★ N273D | 96 | 105 |
|  | N275D, K277E | 122 | 108 |
| site D | ★ H110K | 99 | 104 |
|  | ★ I114T | 89 | 103 |
|  | ★ Q169E | 89 | 111 |
| Binding Site | Q222L, G224S | 94 | 104 |

Table 4: Mutagenesis of Viet04 H5 HA to locate Ab epitopes at one of five antigenic sites (A-E) on HA1 (see FIG. 1). Binding of Abs to mutate H5 HA was scored as a % of binding to Viet04 Wt protein. Mutations that reduce Ab binding to below 85% of Wt HA (highlighted orange) were considered significant for the purposes of epitope identification. Binding data were acquired by cell-based ELISA, as described in the methods. Mutations to residues within the Ab 1A2 and 5C5 epitopes, as determined in the 1A2/H5 and 5C5/H5 crystal structures, are indicated by an empty and full star, respectively.

The interface spans a distance of almost 40 Å from Thr167 to Asn273 at the base of the vestigial esterase domain, and buries a large solvent-accessible surface area of approx. 2,046.8 Å$^2$, as compared to approx. 1,500 Å$^2$ commonly observed for protein-antibody interactions (Wilson and Stanfield (1994) Curr Opin Struct Biol 4, 857). The epitope is conformational, comprising the β-strand His110-Ile116, three loop regions (Gly46-Arg53, Asp68-Glu75 and Thr167-Glu170), as well as Asp43, Tyr164, Tyr 271 and Asn273. The interface is coordinated primarily by contacts with polar residues, involving 13 hydrogen bonds, 4 of which are mediated by bridging water molecules.

All six complementarity determining region (CDR) loops of 1A2 Fab are involved in the interaction, as well as residues within the conserved Framework Region 3 of the immunoglobulin light chain (FRL3), with the majority of the buried surface area (60%) mediated by residues within the Fab heavy chain (VH). Three polar residues on HA1, Asn72, Glu112 and Gln169, account for almost 30% of the surface area within the interface and mediate 6 of 13 inter-molecular hydrogen bonds. Interaction with CDR L3 is limited to contacts with only a single residue, TyrL90, which forms the roof of a small cavity between the heavy and light chains of 1A2 bordered by AsnL32, TyrL49, SerL50 and AsnH100, into which the side chains of Glu112 and Lys255 are inserted. The outwards-facing side chain of Asn72 is at the heart of the 1A2 epitope, and lies directly within the turn formed at the tip of the hairpin structure of CDRH3 to hydrogen bond with GlyH96 and GlyH99. Asn168, Gln169 and Glu170 form contacts with SerL50 and HisL53 in CDR L2, GluL66 and GlyL68 in FRL3 and GlyL30 and AsnL32 in CDRL1, respectively. The 1A2 epitope includes five residues (Ile71-Glu75) equivalent to antigenic site Cb, as well as three residues (Thr167-Gln169) equivalent to Ca (see FIG. 6).

Comparison of H5 HA from the 1A2 Fab-H5 and 5C5 Fab-H5 Complexes

Similarity in the overall topology of H5 HA from the 5C5 and 1A2 complex structures and the un-complexed A/Vietnam/1203/04 HA (PDBID 2FK0) implies 1A2 and 5C5 interaction does not induce large structural changes in the HA1/HA2 per se. However, H5 from the 1A2 complex exhibits a different conformation in Asn60-Gly67 in the B strand of HA2. This loop is shifted by 6 Å towards the helical core of the HA2 domain. This shift is accompanied by a shift in the position of loops comprising residues 270-306 of HA1, located beneath the vestigial esterase domain; the 1A2 epitope is located directly above this region. Crystal lattice contacts and/or antibody interactions that occur in or around this region of the HA1 may account for an outwards movement in residues 270-306, transmitted to the helical core of HA2 through Ile299-Glu301. Temperature (B) factors for these residues are not higher than the average value for the respective structures, and the conformation adopted is common to all HA1/HA2 monomers within a trimer.

Four structures of HA from H5N1 viruses have been reported previously, both in the un-complexed form (Stevens et al. (2006) Science 312, 404; Russell et al. (2006) Nature 443, 45), as well as in complex with Ab Fabs (Ekiert et al. (2009) Science 324, 246; Sui et al. (2009) Nat Struct Mol Biol 16, 265). The crystal structure of an apo-H5 HA from an avian virus (A/Duck/Singapore/3/1997) (PDB: 1JSM) has also been described (Barbey-Martin et al. (2002) Virology 294, 70). Alignment of all five existing H5 structures with the H5 component of the 5C5 and 1A2 complex structures indicates all seven structures have a highly similar overall topology in the receptor-binding domain, as well as in the membrane-proximal regions of the HA1 and HA2. However, all seven H5 HA structures exhibit one of the two distinct conformations in the loops comprising residues Asn60-Gly67 in the B strand of HA2, suggesting these residues are not inherently flexible, but adopt one of two distinct conformations. The significance of this conformational dichotomy, which is independent of the pH of crystallization, is unclear and awaits further investigation. With regards to this distinction in the HA2, our 1A2 complex structure, crystallized at pH 5.6, is more similar to the un-complexed A/Vietnam/1194/04 structure crystallized at pH 6.5 (PDB: 2IBX) and the A/Vietnam/1203/04 H5, crystallized at pH 6.0 (PDB: 3GBM) in complex with a nAb Fab which prevents the process of membrane fusion. HA from our 5C5 complex, crystallized at pH 8.0, is more similar to the un-complexed A/Vietnam/1203/04 structure crystallized at pH 6.6 (PDB: 2FK0,) and the Viet04 ectodomain crystallized at pH 8.5 (PDB: 3FKU) in complex with a nAb Fab which prevents the process of membrane fusion. RMSD values for superimposition of the H5 HA from the 1A2/HA and 5C5/HA complexes is 1.92 Å for 485 Cα atoms (314/171 in HA1/HA2, respectively). RMSD values were calculated using a least squares algorithm, as implemented within Coot. Of the pre-existing H5N1 HA structures, H5 from the 1A2 complex has the highest degree of complimentarily with the H5 HA ectodomain crystallized at pH 6.5 (PDB: 2IBX). In contrast, H5 from the 5C5 complex, crystallized at pH 8.0, shows greater structural complementarity with the H5 ectodomains crystallized at pH 8.0 (PDB: 2FK0) and pH 8.5 (PDB: 3IBX). Alignment reveals subtle structural differences within loop regions at the base of the eight-stranded beta-sheet structure of HA1. Of note, Asn60-Gly67 in the B strand of HA2 is shifted towards the HA2 C strand and the a-helical core of the trimer in those structures crystallized at or below pH 6.5 relative to those crystallized at neutral pH. This shift is accompanied by a shift in the loop comprising 270-306 of HA1 that induces a subtle change in the position of loops in this region of HA1, suggesting pH-associated variation in between HA1 and HA2 domains. In this regard, it is possible that the neutralizing effects of antibodies that bind to antigenic site E are in part due to stabilization of the pre-fusion HA1/HA2 complex.

Mechanism of Neutralization by 1A2 and 5C5

Figure 7C:
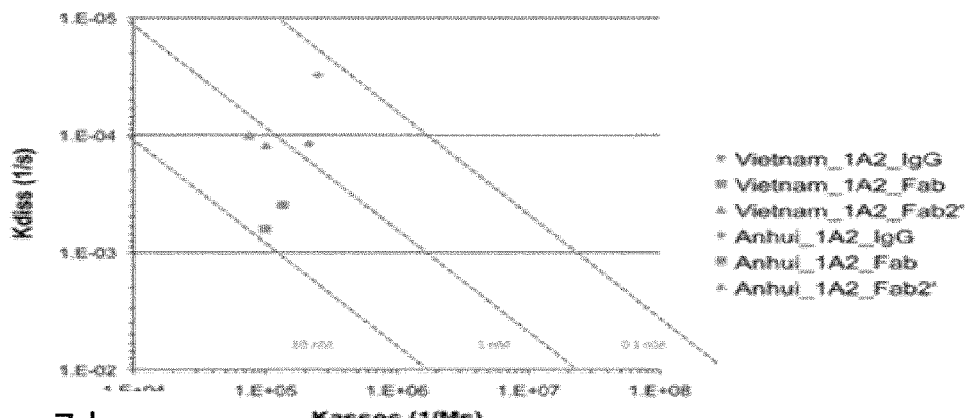
FIG. 7: Investigation of the molecular basis for neutralization of H5 viruses by 5C5 and 1A2. Live viruses used in this assay were produced as follows; VN1203: RG-A/Vietnam/1203/04-PR8, Anhui/5: RG-A/Anhui/5/2005-PR8, Indo/05: A/Indonesia/5/2005-PR8, Pheasant/NJ: RG-A/Pheasant/New Jersey/4/93-PR8, Brisbane/59: RG-A/Brisbane/59/2007-PR8. A) Haemagglutinin-Inhibition (HI) assay for IgG, Fab2' and Fab fragments of 1A2 and 5C5. HI data are expressed as the inverse titres per 0.1 mg/ml antibody/Fab2'/Fab, respectively. A result with no agglutination inhibition is indicated by a hyphen. B) Microneutralization assay (MN) for IgG, Fab2' and Fab fragments of 1A2 and 5C5. MN data are expressed as the titres inverse of endpoint of dilution) per 80 µg/ml antibody/Fab2'/Fab; titres <16 are considered to represent a lack of MN activity. For calculation of concentration, IgG was considered as having MW=150 kDa, Fab2'=100 kDa and Fab=50 kDa. C) Affinity $k_{dissoc}/k_{assoc}$ isotherm plots for 1A2 and D) 5C5 IgG, Fab and Fab2' molecules binding to recombinant HA of Viet04 and Anhui05, respectively. Biolayer interferometry measurements were performed using an Octet Red (Fortebio Inc.). E) Protease protection assay, as described in the methods. Non-reducing SDS-PAGE of Viet04 HA at pH 5 or pH 8, incubated with nabs 5C5 or 1A2 or alone, with or without trypsin. Tryptic digestion of Viet04 HA at pH 5.0 in the presence of Abs 1A2 and 5C5 precludes neutralization by prevention of low pH-induced conformational changes in HA2.
Figure 7D:
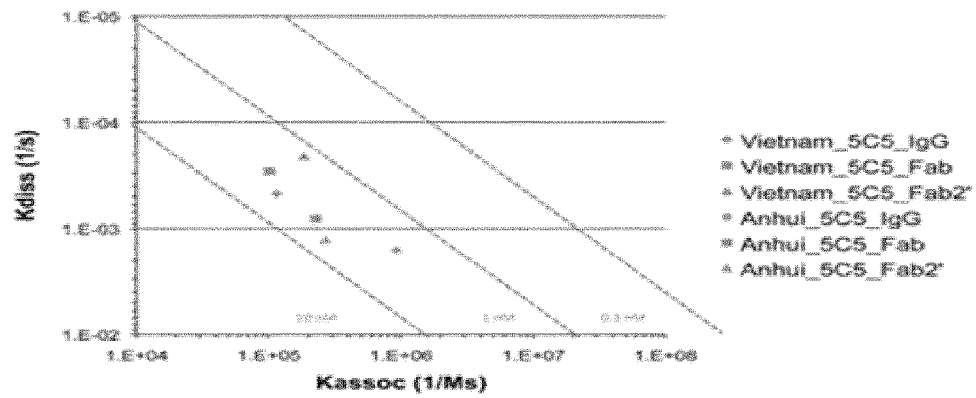
Figure 7E:
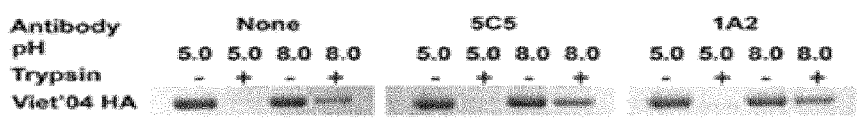

Spatial separation of the 1A2 and 5C5 epitopes, MN and HI data all imply neutralization by distinct mechanisms. Binding of 5C5 to the sialic acid binding site inhibits interaction with host receptors, preventing viral attachment to the host cell. This is the predominant mechanism of neutralization for nAbs that bind to antigenic sites Ca, Cb and Sa in H1N1 viruses (A and B in H3N2 viruses). Such mAbs have previously been structurally characterized in complex with HAs from H3 (Bizebard et al. (1995) Nature 376, 92) as well as H1 (Xu et al. (2010), Science 328, 357; Whittle et al. (2011) Proc Natl Acad Sci USA) viruses. The mechanism of neutralization by 1A2 is less clear. Located within the vestigial esterase domain at a distance from the sialic acid binding site, the closest residue in 1A2 Fab (AsnH97) is about 22 Å away from a sialic acid moiety modeled within the receptor binding site. Our structural data demonstrate steric blockade of HA receptor binding by 1A2 does not occur in the context of Fab alone, and could only occur through indirect occlusion of the RBD by the intact 1A2 IgG or Fab2'. Moreover, neutralizing activity based on inhibition of receptor binding by 1A2 must occur independently of that required for H1 (Table 1). Abs that do not block the receptor-binding function of HA elicit neutralization by inhibition of the pH-dependent conversion of H5 HA from the pre-fusion to post-fusion form (Sui et al. (2009) Nat Struct Mol Biol 16, 265; Barbey-Martin et al. (2002) Virology 294, 70; Okuno (1993) J Virol 67, 2552; Throsby et al. (2008) PLoS One 3, e3942). However, 1A2 does not prevent this pH-dependent conformational change (FIG. 7E). To probe the mechanism of neutralization by 1A2 we produced Fab and Fab2' fragments of 1A2 and 5C5, for H1 and MN assays. Measurement of the kinetics of interactions using biolayer interferometry confirmed that all three species of both nAbs bound to recombinant HA with nano-molar affinities (FIG. 7C, D). HI assays using a panel of H5 viruses from diverse lineages indicated that, in contrast to 5C5, 1A2 interaction does not prohibit agglutination of red blood cells, consistent with the notion that nAbs binding to antigenic site E do not inhibit the sialic acid-binding function of HA per se (FIG. 7A). MN assays using multiple clades of H5 viruses demonstrated that 1A2 IgG and Fab2' both elicit neutralization, whereas 1A2 Fab did not (FIG. 7B). Hence, neutralizing activity is associated with either the bivalent nature of virus-antibody interaction, or the larger size of the IgG/Fab2' relative to Fab. Notably, intact IgG (~150 kDa) neutralized infectivity at a lower concentration than the smaller Fab2' (~100 kDa), which was in turn more efficient than the Fab (~50 kDa), indicating molecular size is significant for the process of neutralization. Hence, the mechanism of neutralization by 1A2 is likely due to inhibition of viral attachment by steric blockade of the receptor-binding function of adjacent HA trimers, such that antibodies bound to HA at the viral surface inhibit receptor-binding of neighboring HA trimers, due to relatively large size of the 1A2 antibody or Fab2'. Previous studies, which examined the structural and binding characteristics of neutralizing antibodies that interacted with an equivalent region of the H3 HA, arrived at the same conclusions regarding the mechanism of neutralization by these antibodies, based upon affinity and avidity measurements of IgG and Fab interactions in vitro (Fleury et al. (1999) Nat Struct Biol 6, 530; Fleury et al. (2000) Proteins 40, 572; Knossow et al. (2002) Virology 302, 294).

Figure 6:
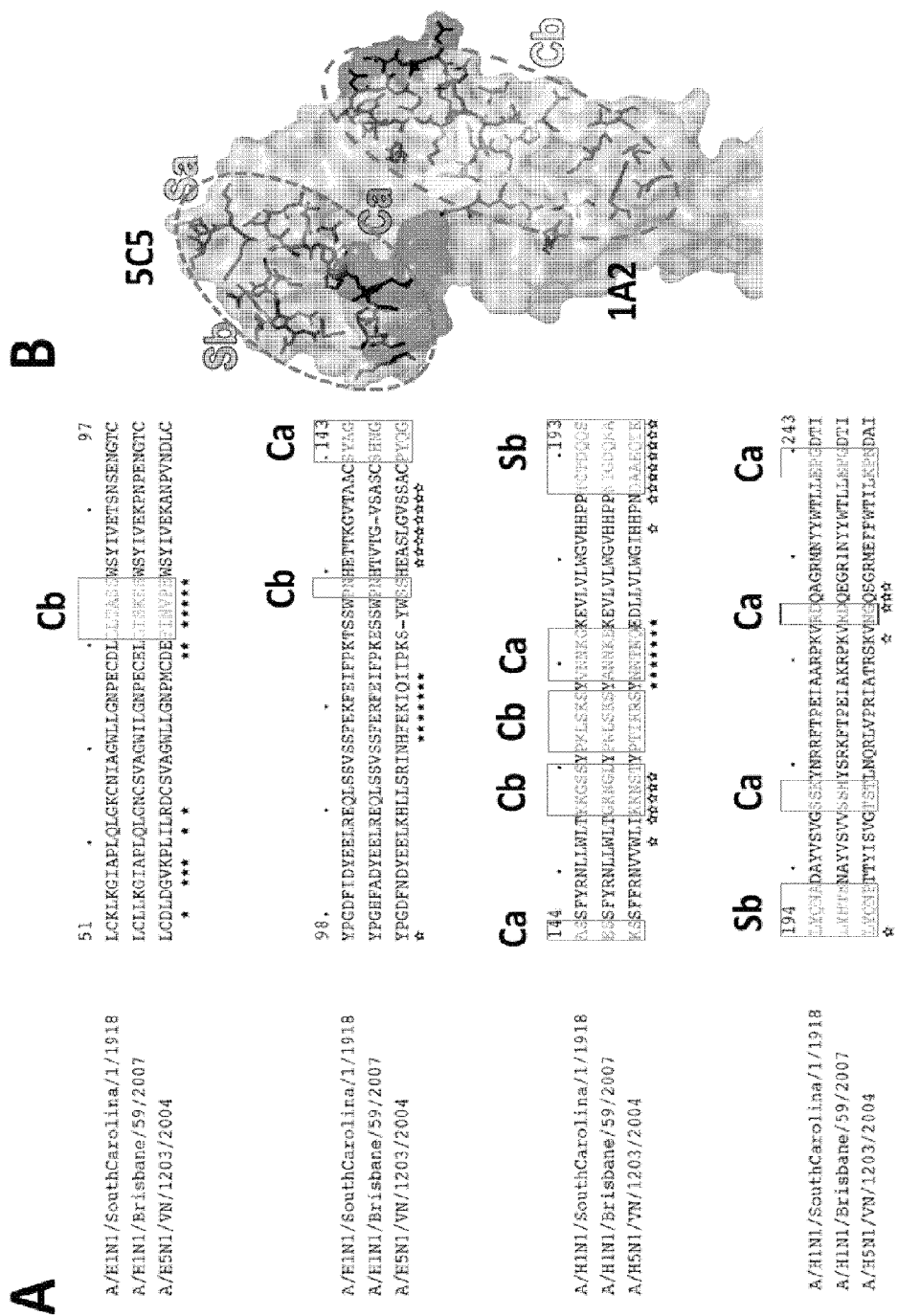
FIG. 6: Antigenic sites of H1 and H5 HAs. A) Sequence alignment of H1 (A/SouthCarolina/1/1918 and A/Brisbane/59/2007) with H5 (A/Vietnam/1203/04) illustrates a high degree of sequence similarity between the H1 and H5 subtypes (SEQ ID NOS: 12-14, respectively, in order of appearance). Antigenic sites (Sa, Sb, Ca and Cb) are labelled and indicated as boxed, light gray text and residues within the 5C5 and 1A2 epitopes are highlighted by open and solid stars, respectively. B) A surface representation of the HA1/HA2 from H1N1 HA (PDB: 1RD8 (Stevens et al. (2004) Science 303:1866), depicts the relative locations of the antigenic sites identified in H1 viruses (Sa, Sb, Ca and Cb) on the surface of H5 HA. Residues spatially equivalent to those within the 1A2 and 5C5 epitopes are indicated as sticks and encircled. The H1 antigenic sites are shaded and labelled.

Currently, antigenic variation amongst influenza viruses following sustained circulation amongst humans is only well-established in the context of H1 and H3 strains. Comparison of H5 HA with the structurally homologous H1 HA indicates both 5C5 and 1A2 epitopes comprise regions equivalent to highly-variant antigenic sites in H1 HA (FIG. 6). Hence, both epitopes may be subject to stronger selective pressure in the context of a pandemic H5 virus if the established antigenic variability amongst H1 viruses would be translated to structurally-equivalent positions of H5 viruses upon sustained circulation amongst humans. Nevertheless, our data showed both Abs neutralized multiple clades of H5 viruses in vitro, and provided complete prophylactic and therapeutic protection against Viet04 infection in vivo, indicating the efficacy of these Abs against contemporary HPAI viruses.

Figure 8:
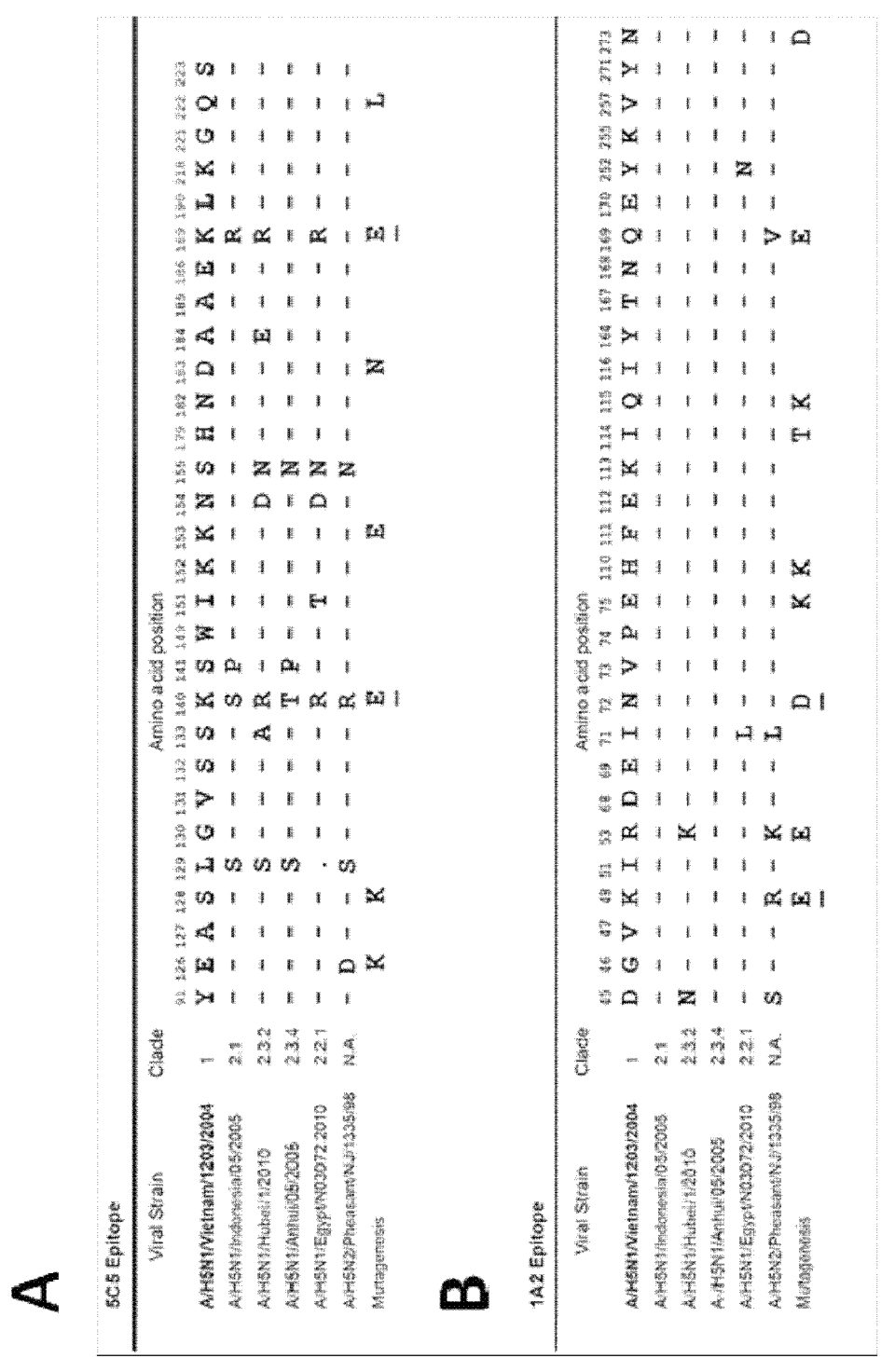

In summary, 5C5 binds directly over the RBD (FIG. 4A) and its epitope comprises components of all the canonical elements of the sialic acid binding site (RBS), including the 130-loop, the 220-loop, the 180-alpha helix, as well as the nearby 150-loop. The epitope is restricted to a single HA monomer and is immediately adjacent to the N-glycosylation site at Asn154 (FIG. 4B). 1A2 binds further away from the RBD (FIG. 4C) and spans the beta-sheet structure at the base of the vestigial esterase domain (FIG. 4D). Both epitopes are restricted to the HA1 and are spatially distinct from that of 7B8, which also comprises HA2. Residues within the 5C5 and 1A2 epitopes are conserved amongst geographically and temporally diverse H5 viruses (FIG. 8).

The 5C5 and 1A2 epitopes define two novel conserved surface patches amongst contemporary H5 viruses. Both Abs exhibit neutralizing activity in the presence of multiple residue substitutions within these epitopes (FIG. 8), demonstrating capacity to tolerate mutation.

Mutagenesis of the H5 HA1 identified single amino acid substitutions that could disrupt 5C5 or 1A2 interactions in vitro (Table 4, FIG. 1), however it is unclear whether such substantial changes in topology and charge would be permissive in vivo, particularly in the RBS component of the 5C5 epitope. Moreover, dramatic variation in size and charge of five residues at the periphery of the 5C5 epitope and eight residues within the 1A2 epitope (Table 4) did not adversely affect Ab interactions, consistent with limited inter-molecular contacts formed by these residues. Hence, recognition of multiple clades of H5 viruses by 5C5 and 1A2 reflects conservation amongst the critical elements of both epitopes, coupled with tolerance for residue substitutions amongst the peripheral components.

The co-crystal structure of 5C5 indicates that the antibody blocks H5 HA interaction with host receptors, preventing viral attachment to the host cell and providing highly-effective neutralization of infection, which exceeds that of 1A2 (Table 1, FIG. 7B). Conservation in the RBS amongst H5 viruses enables broad-spectrum neutralization by 5C5 (FIG. 8A). Antibodies to the RBS of H1 HA also elicit cross-clade neutralization (Whittle et al., Proc Natl Acad Sci USA 108, 14216). Reduced binding of 5C5 to A/Egypt/N03072/2010 is possibly associated with a deletion at position 129, which is a feature shared by clade 2.2.1 H5 viruses (Cattoli et al., J Virol 85, 8718).

Sustained person-to-person transmission of H5 HPAI would likely require changes within the RBS to enhance binding of sialic acid-α2-6-galactose structures; e.g. Gln222Leu and Gly224Ser (226/228 in H3 numbering). However, if these changes were to alter the 5C5 epitope and eliminate recognition by nAb 5C5, its appeal for pandemic mitigation would be lost. Interestingly, the reactivity of nAb 5C5 with a double mutant Viet04 HA bearing these RBS changes was not affected (Table 4), suggesting that the eventual pandemic virus should remain susceptible to neutralization by 5C5. The mechanism of neutralization by 1A2 is unclear; indirect inhibition of receptor binding or membrane fusion seem possible (FIG. 7). The 1A2 epitope, located closer to the viral membrane in the vestigial esterase domain is more highly-conserved amongst H5 HA than the 5C5 epitope, which is thought to mutate to escape neutralizing antibody responses (FIG. 8). The conservation of 1A2 epitope could be attributed to reduced immunogenicity or, less likely, to unknown functional constraints promoting conservation (FIG. 5). The notion that the vestigial esterase domain comprises an accessible surface that is less immunodominant than the highly-exposed tip of HA1 is supported by the finding that structurally-equivalent surface patches of contemporary (2000-2011) H1 and H3 viral subtypes are also highly conserved (>99%), as compared to binding sites A (97% and 93%) or B (92% and 93%), in these subtypes, respectively (FIG. 5B-D). In this regard, nAbs that bind the vestigial esterase region of HA1 have potential to be less vulnerable to antigenic drift and mediate homo-subtypic protection against divergent clades.

Our studies indicated protective efficacy of neutralizing Ab epitopes correlated positively with distance from the viral membrane, whereas conservation correlated inversely; Abs against the exposed tip of the HA afford the most potent protection to a narrow range of viruses. Ab 5C5 may be an exception by mimicking the host receptor to engage with the conserved RBS in HA. In contrast, nAbs binding membrane-proximal epitopes provide broadly-cross reactive, longer-term protection but reduced potency. Hence, therapeutic strategies using a combination of nAbs such as 5C5, 1A2 described here and nAb 7B8 to the fusion peptide could exploit the spatial and mechanistic diversity between these three neutralizing epitopes (FIG. 5A), to reduce concerns about emergence of immune escape mutants in the population before effective pandemic vaccines can be produced.

Example 9: Carbohydrate Blockade of Surface Patches

To test Ab reactivity to CHO mutants (see FIG. 1b) we assessed binding of 1A2 (binds to site E, in the vestigial esterase domain) and 5C5 (binds to site A/B in the globular head) to mutant HA1 proteins containing single or multiple additional N-carbohydrates (CHO), using ForteBio.

Single and multi-CHO HA1 proteins were produced on a soluble, His-tagged wild type (WT) VN HA1 backbone. Five days post-infection, recHA was purified from tissue-culture supernatant using Ni-NTA beads. Protein eluted from the beads was concentrated to ~100-200 µl and analyzed by SDS-PAGE. All CHO mutants were expressed at equivalent levels and ran as a single band with MW higher than the WT species.

For the determination of mAb accessibility, all samples were diluted to an equivalent conc. of 100 µg/ml using ForteBio kinetics binding buffer (PBS w. BSA). All samples were bound to bio-sensors for 1 hr and then probed with a solution containing either 5C5 or 1A2 IgG (10 µg/ml), The binding to the following variants was tested in the experiment (all numbering is based upon the mature HA protein):

| | | |
|---|---|---|
| 1. | CHO6A | (Lys119Asn - NSS) |
| 2. | CHO6B | (Ser121Asn - NWS) |
| 3. | CHO7 | (Glu126Asn - NAS) |
| 4. | CHO8B | (Gln192Asn, Pro194Ser - NNS) |
| 5. | CHO8D | (Pro194Asn - NTT) |
| 6. | CHO9 | (Asn 240; Glu242Ser - NFS) |
| 7. | Vietnam Wt (HA1) | |
| 8. | CHO2/7/8 HA1 | (Asn140, Asn126, Asn 194) |
| 9. | CHO2 | (Lys140Asn - NSS) |
| 10. | Blank | |

Figure 9:
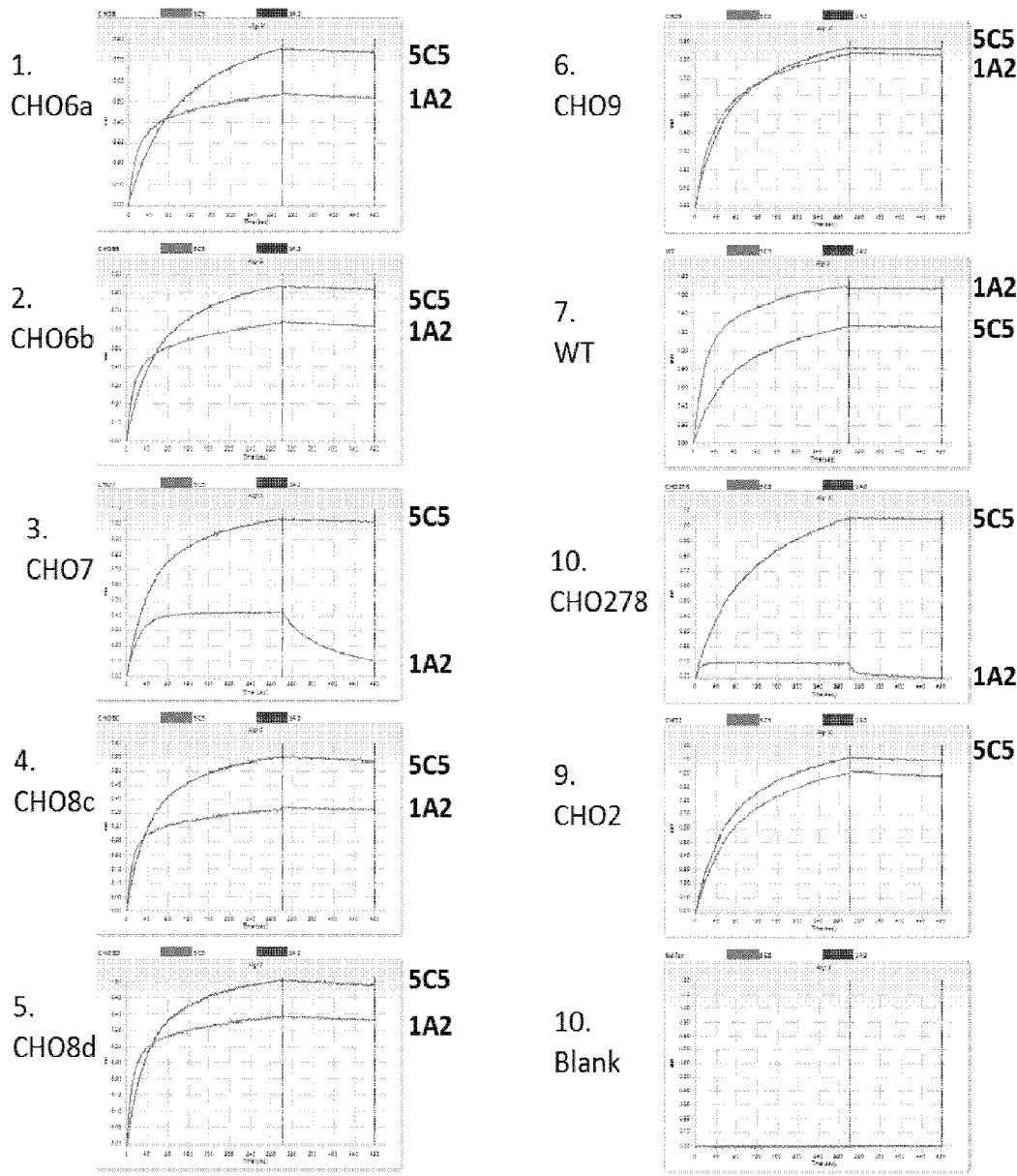
FIG. 9: Fortebio-based analyses of the effect of individual CHO mutants on 1A2 and 5C5 interactions. 5C5 reactivity and 1A2 reactivity are depicted. Immobilized CHO/Wt HA1 was used as antigen.

CHO2,7,8D inhibited 5C5 but not 1A2 (FIG. 9). Results of binding and dissociation in real time indicated that only CHO7 significantly reduced 5C5 interaction, although this protein bound 1A2 equivalent to WT, and the effect was only truly visible in the dissociation kinetics, in which it was apparent the Ab did not bind with nm affinity, but came off almost completely following the association phase. This pattern was distinct from that observed in CHO278, whereby the 5C5 Ab barely bound at all, implying that although CHO7 is responsible for interference of robust IgG interaction, the presence of other mutants (CHO8 and CHO2) also provide further obstruction to Ab binding (FIG. 9).

Hyperglycosylated Variant HA to Focus Immune Responses to the 1A2 Epitope

The data in FIG. 9 show that a CHO HA1 that displays the 1A2 epitope and excludes other epitopes in and around the highly-antigenic globular head can be made using the CHO2,7,8D multi-CHO HA1 construct, as this shows high reactivity to 1A2 and no reactivity to 5C5. The lack of the HA stalk in this construct precludes immune response to this component.

Hyperglycosylated Variant HA to Focus Immune Responses to the 5C5 Epitope

To design a CHO HA1 that specifically displayed the 5C5 epitope, we needed to exclude all other epitopes around the HA1, including the region of the 1A2 epitope. A number of constructs were generated that included an additional glycosylation position Asn 72 (mutation of Pro at position 74 to Ser), which abrogated Ab binding here. Following results of combinatorial CHO mutants screened for good expression, we identified CHO mutant CHO2,4,6,CAASP, to mask all non-5C5 reactive regions of the HA1. This construct was expressed and used in Fortebio experiments to determine the binding characteristics of this construct with respect to Ab recognition. Results showed that CHO2,4,6,CAASP inhibited 1A2 binding, but also reduced 5C5 reactivity somewhat relative to wild-type (data not shown). These data provide a proof-in-principle that carbohydrate masking of HA epitopes may be used to exclude immune responses against any given region of the HA. Lack of the HA stalk in this construct precludes immune response to this component.

Hyperglycosylated Mutants HA to Focus Immune Responses to the 7B8 Epitope

Design of an HA variant that specifically displays the 7B8 epitope, the full-length construct needs to be included, in order to incorporate the 7B8 epitope in the membrane-proximal stalk region of HA. Given the Ab 5C5 inhibition demonstrated by the CHO2,7,8D multi-CHO HA1 (FIG. 1) and inhibition of 1A2 by the CAASP mutant (FIG. 2), a full-length construct comprising CHO2,7,8D,CAASP will effectively mask reactivity of Abs to the head (i.e. 5C5-like) and also to the vestigial esterase domain (i.e. 1A2-like), leaving the 7B8 binding region within the stalk exposed for immune surveillance.

Example 10: Analyses for the Identification of Equivalent Conserved Antibody-Accessible Surface Patches (CAASP) on Other HA Subtypes The concept of carbohydrate-mediated occlusion of the more variable components of the H5 HA can be extended to subtypes outside of H5. To this end, we analyzed the conservation of surface residues amongst viruses from the following;

1. Subtype H1 (global, circulating in humans 2009-present)
2. Subtype H7 (Asian, circulating amongst avian species)
3. Subtype H7 (North American/European, circulating amongst avian species)
4. Subtype H9 (global, circulating amongst avian species)

These analyses have identified invariant surfaces (i.e. against which a cross-protective immune response may be generated) as well as non-conserved surface residues, which may be masked by the presence of additional N-carbohydrates to prevent immune recognition of these areas.

Method: The sequence of the HA1 component of viruses from subtypes human H1pdm, H7 (avian/human) and H9 (avian/human) were downloaded from the GISAID database (on Sep. 11, 2012), aligned and assessed for sequence divergence at each amino acid positions. The number of amino acid substitutions at each given position was calculated using as a percentage of the total using the program. A cut-off value of >99% conservation at each position was used to determine the CAASP for each subtype. These residues were mapped onto the structure of the respective HA subtypes (H1, PDB ID 3M6S; H7, PDB ID 1TI8; PDB ID 1JSD) and displayed using the program Pymol.

The CAASP identified amongst H1 viruses (2009-2012) is large, comprising ~340 residues, with only 47 residues defined as non-CAASP. These residues are listed below;

H1 CAASP (Global, 2009-2012)

All residues within the HA1 component of the mature protein, including residues numbered:
1, 2, 3, 4, 5, 6, 7, 8, 9, 10, 11, 12, 13, 14, 15, 16, 17, 18, 20, 21, 23, 24, 25, 26, 27, 28, 29, 30, 33, 34, 36, 37, 38, 39, 40, 41, 42, 43, 44, 45, 46, 48, 49, 50, 51, 52, 53, 54, 55, 57, 58, 59, 60, 61, 62, 63, 64, 65, 66, 67, 68, 69, 70, 71, 72, 73, 74, 75, 76, 77, 78, 79, 80, 81, 82, 85, 87, 88, 89, 90, 91, 92, 93, 94, 95, 96, 98, 99, 100, 101, 102, 103, 104, 105, 106, 107, 108, 109, 110, 111, 112, 113, 114, 115, 117, 118, 120, 122, 123, 124, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 217, 218, 219, 220, 221, 222, 223, 224, 225, 226, 227, 228, 229, 230, 231, 232, 233, 234, 236, 237, 238, 239, 240, 241, 242, 243, 244, 245, 246, 247, 248, 249, 250, 251, 252, 253, 254, 255, 256, 257, 258, 259, 261, 262, 263, 264, 265, 266, 267, 268, 269, 270, 271, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 321, 323, 324, 325, 326, 327, 328 and 331

The CAASP identified amongst H7 and H9 viruses circulating amongst avian species is smaller than that of recent human H1 viruses. Given the broad geographic diversity amongst strains within the H7 subtype, H7 viruses are divided into two groups for the purposes of CAASP identification; (1) Viruses isolated in Asia and (2) viruses isolated in Europe and/or North America. Residues identified as the CAASP within each group of viruses are listed below for each group, respectively;

H7 CAASP (Asia)

Residues within the HA1 component of the mature protein numbered:
1, 2, 3, 4, 5, 6, 7, 8, 9, 10, 12, 13, 15, 16, 18, 19, 20, 21, 23, 25, 26, 29, 30, 31, 32, 33, 34, 39, 41, 42, 45, 46, 50, 51, 53, 54, 55, 56, 57, 58, 59, 62, 63, 64, 65, 66, 67, 69, 70, 71, 72, 73, 74, 76, 77, 79, 80, 81, 83, 85, 87, 88, 89, 90, 91, 92, 94, 96, 98, 99, 100, 102, 103, 105, 106, 107, 108, 110, 111, 115, 116, 117, 122, 124, 126, 129, 131, 135, 136, 137, 138, 139, 140, 142, 143, 144, 145, 149, 152, 153, 154, 156, 157, 158, 159, 161, 166, 167, 168, 169, 171, 172, 173, 174, 175, 176, 178, 181, 182, 185, 186, 187, 189, 191, 192, 193, 194, 195, 197, 198, 200, 202, 203, 204, 206, 211, 212, 213, 215, 216, 217, 218, 219, 220, 221, 223, 224, 225, 228, 231, 232, 233, 235, 236, 237, 238, 239, 240, 241, 242, 243, 244, 245, 247, 250, 251, 253, 254, 255, 257, 258, 259, 260, 263, 265, 268, 270, 272, 273, 276, 277, 278, 279, 281, 283, 284, 285, 286, 287, 288, 289, 290, 291, 294, 296, 297, 299, 300, 302, 304, 305, 307, 308, 309, 310, 311, 312, 313, 314, 315, 316, 325, 326, 327, 328 and 331.

H7 CAASP (Europe/North America)

Residues within the HA1 component of the mature protein numbered:
1, 2, 3, 4, 5, 6, 7, 8, 9, 10, 12, 13, 14, 16, 18, 19, 20, 21, 23, 25, 26, 27, 28, 29, 30, 31, 32, 33, 34, 41, 42, 45, 46, 50, 51, 52, 54, 55, 57, 58, 62, 63, 64, 65, 66, 67, 69, 70, 71, 72, 76, 77, 79, 80, 82, 83, 85, 87, 88, 89, 90, 92, 94, 95, 96, 98, 99, 100, 101, 102, 103, 105, 106, 107, 110, 111, 114, 115, 116, 117, 119, 121, 122, 123, 124, 127, 129, 131, 134, 135, 136, 137, 138, 139, 140, 141, 142, 143, 144, 145, 146, 149, 150, 153, 154, 155, 160, 162, 167, 168, 169, 170, 172, 173, 175, 176, 177, 179, 182, 183, 184, 186, 187, 188, 190, 192, 193, 196, 198, 199, 200, 201, 203, 204, 205, 207, 210, 212, 221, 222, 223, 224, 226, 229, 232, 233, 234, 235, 236, 237, 239, 240, 241, 242, 243, 244, 245, 246, 248, 249, 251, 254, 256, 258, 260, 261, 266, 269, 271, 273, 275, 277, 278, 279, 280, 282, 284, 285, 286, 287, 288, 289, 290, 292, 295, 297, 298, 299, 300, 301, 303, 305, 306, 308, 309, 310, 311, 312, 314, 316, 317, 329 and 332.

H9 CAASP (Global)

Residues within the HA1 component of the mature protein numbered:
1, 2, 3, 4, 5, 6, 8, 9, 10, 11, 12, 13, 14, 15, 16, 17, 18, 19, 21, 23, 25, 26, 27, 31, 32, 33, 35, 36, 37, 38, 39, 40, 41, 42, 43, 44, 47, 49, 50, 51, 52, 54, 55, 58, 59, 60, 62, 63, 64, 65, 67, 71, 73, 76, 77, 78, 79, 80, 81, 82, 84, 85, 88, 90, 91, 92, 93, 96, 97, 98, 99, 100, 101, 102, 105, 106, 107, 110, 111, 117, 118, 119, 122, 123, 124, 128, 129, 130, 133, 134, 137, 138, 139, 141, 142, 143, 144, 145, 151, 152, 154, 155, 156, 157, 158, 159, 160, 166, 167, 168, 170, 171, 172, 175, 177, 181, 184, 185, 189, 190, 192, 196, 197, 201, 203, 204, 205, 208, 209, 210, 211, 215, 218, 219, 222, 223, 224, 227, 228, 229, 230, 231, 232, 233, 234, 236, 237, 239, 240, 241, 242, 243, 244, 245, 247, 248, 250, 252, 254, 255, 256, 257, 259, 260, 263, 266, 268, 270, 271, 272, 273, 274, 275, 277, 278, 279, 280, 282, 283, 284, 285, 287, 289, 290, 291, 292, 293, 294, 296, 298, 299, 304, 305, 306, 307, 308, 310, 312, 313, 314, 315 and 320.

Based on the data set forth within the experimental results above, masking of regions of the HA1 of various influenza subtypes with additional Asn-linked carbohydrates to direct immune responses to highly-conserved epitopes (CAASP regions) may be achieved as follows;

For targeting of the immune response to the CAASP regions of the HA from H1 viruses circulating amongst the human population globally from 2009-present, additional Asn-linked glycosylation could be introduced at positions 19, 22, 31, 32, 35, 47, 56, 83, 84, 86, 97, 116, 119, 121, 125, 134, 138, 141, 143, 155, 156, 162, 163, 183, 185, 186, 197, 203, 205, 215, 216, 235, 260, 272, 309, 310, 311, 312, 313, 314, 315, 316, 317, 318, 319, 320 or 322 of the HA1 component of the mature protein.

For targeting of the immune response to the CAASP regions of the HA from H7 viruses circulating amongst avian species in Europe and/or North America, additional Asn-linked glycosylation could be introduced at positions 11, 14, 17, 22, 24, 27, 28, 60, 61, 35, 36, 37, 38, 40, 43, 44, 47, 48, 49, 52, 68, 75, 78, 82, 84, 86, 93, 95, 97, 101, 104, 109, 112, 113, 114, 118, 119, 120, 121, 123, 125, 127, 128, 130, 132, 133, 134, 141, 146, 147, 148, 150, 151, 155, 160, 162, 163, 164, 165, 170, 179, 180, 183, 184, 188, 190, 196, 199, 201, 205, 207, 208, 209, 210, 214, 222, 226, 227, 229, 230, 234, 246, 248, 249, 252, 256, 261, 262, 264, 266, 267, 269, 271, 274, 275, 280, 282, 292, 293, 295, 298, 301, 303, 306, 317, 318, 319, 320, 321, 322, 323, 324, 329 or 330 of the HA1 component of the mature protein.

For targeting of the immune response to the CAASP regions of the HA from H7 viruses circulating amongst avian species in Asia, additional Asn-linked glycosylation could be introduced at positions 11, 14, 22, 24, 27, 28, 35, 36, 37, 38, 40, 43, 44, 47, 48, 49, 52, 60, 61, 68, 75, 78, 82, 84, 86, 93, 95, 97, 101, 104, 109, 112, 113, 114, 118, 119, 120, 121, 123, 125, 127, 128, 130, 132, 133, 134, 141, 146, 147, 148, 150, 151, 155, 160, 162, 163, 164, 165, 170, 177, 179, 180, 183, 184, 188, 190, 196, 199, 201, 205, 207, 208, 209, 210, 214, 222, 226, 227, 229, 230, 234, 246, 247, 248, 249, 250, 251, 252, 256, 261, 262, 264, 266, 267, 269, 271, 274, 275, 280, 282, 292, 293, 295, 298, 301, 303, 306, 317, 318, 319, 320, 321, 322, 323, 324, 329 or 330 of the HA1 component of the mature protein.

For targeting of the immune response to the CAASP regions of the HA from H9 viruses circulating globally amongst avian species, additional Asn-linked glycosylation could be introduced at positions 7, 20, 22, 2428, 29, 30, 34, 45, 46, 48, 53, 56, 57, 61, 66, 68, 69, 70, 72, 74, 75, 83, 86, 87, 89, 94, 95, 103, 104, 108, 109, 112, 113, 114, 115, 116, 120, 121, 125, 126, 127, 131, 132, 135, 136, 140, 146, 147, 148, 149, 150, 153, 161, 162, 163, 164, 165, 169, 173, 174, 176, 178, 179, 180, 182, 183, 186, 187, 188, 191, 193, 194, 195, 198, 199, 200, 202, 206, 207, 212, 213, 214, 216, 217, 220, 221, 225, 226, 235, 238, 246, 249, 251, 253, 258, 261, 262, 264, 265, 267, 269, 276, 281, 286, 288, 295, 297, 300, 301, 302, 303, 309, 311, 316, 317, 318, 319, 321, 322, 323, 324, 325, 326, 327, 328, 329, 330 or 331 of the HA1 component of the mature protein.

```
Sequence Listing
SEQ ID NO: 1: Amino acid sequence of mature H5 haemagglutinin
from virus A/Vietnam/1203/04 (adapted from NCBI AY818135)
1         10        20        30        40        50        60
DQICIGYHANNSTEQVDTIMEKNVTVTHAQDILEKKHNGKLCDLDGVKPLILRDCSVAGW 61        70        80        90        100       110       120
LLGNPMCDEFINVPEWSYIVEKANPVNDLCYPGDFNDYEELKHLLSRINHFEKIQIIPKS 121       130       140       150       160       170       180
SWSSHEASLGVSSACPYQGKSSFFRNVVWLIKKNSTYPTIKRSYNNTNQEDLLVLWGIHH 181       190       200       210       220       230       240
PNDAAEQTKLYQNPTTYISVGTSTLNQRLVPRIATRSKVNGQSGRMEFFWTILKPNDAIN 241       250       260       270       280       290       300
FESNGNFIAPEYAYKIVKKGDSTIMKSELEYGNCNTKCQTPMGAINSSMPFHNIHPLTIG 301       310       320       330       340       350       360
ECPKYVKSNRLVLATGLRNSPQRERRRKKRGLFGAIAGFIEGGWQGMVDGWYGYHHSNEQ 361       370       380       390       400       410       420
GSGYAADKESTQKAIDGVTNKVNSIIDKMNTQFEAVGREFNNLERRIENLNKKMEDGFLD 421       430       440       450       460       470       480
VWTYNAELLVLMENERTLDFHDSNVKNLYDKVRLQLRDNAKELGNGCFEFYHKCDNECME 481       490       500       510       520       530       540
SVRNGTYDYPQYSEEARLKREEISGVKLESIGIYQILSIYSTVASSLALAIMVAGLSLWM 541       550
CSNGSLQCRICI SEQ ID NO: 2: Amino acid sequence of the variable region of the
heavy chain of mouse IgG 1A2
1         10        20        30        40        50        60
```

-continued

CDRH1 CDRH2

EVQLQQSGPELVKPGASVKMSCKASGYTFTSFIMYWVKQKPGQGLEWLGYIDPYNDGTKY

61 70 80 90 100 110 120

CDRH3

NEKFEGKATLTSDKSSSTAYMELSSLTSEDSAVYYCAKRGNYGNGFAYWGQGTLVTVSAAKTS

SEQ ID NO: 3: Amino acid sequence of the variable region of the light chain of mouse IgG 1A2

1 10 20 30 40 50 60

CDRL1 CDRL2

DIVMTQSQKFVST SVGDRVSVTCKASQNVGSNVAWYQHKPGHSPTALIYSASHRYSGVPD 61 70 80 90 100 110

CDRL3

RFTGSESGTDFTLTISNVQSEDLAEYFCQQYYSYPYTFGGGTKLEIKRADAAPT

SEQ ID NO: 4: Amino acid sequence of the variable region of the heavy chain of mouse IgG 7B8

1 10 20 30 40 50 60

CDRH1 CDRH2

QVQLQQSGAELVRPGTSVKISCKASGYAFSNYWLGWVKQRPGHGLEWIGDIYPGSGNNHY

61 70 80 90 100 110 120

CDRH3

NEKFKGKATLTADKSSRTVYMQLSSLTSEDSSVYFCTRGPIFTTAWFAYWGQGTLVTVSAAQKQTW

SEQ ID NO: 5: Amino acid sequence of the variable region of the light chain of mouse IgG 7B8

1 10 20 30 40 50 60

CDRL1 CDRL2

DIVMTQSQKFMSTSVGDRVSVTCKASQNVDTYVAWYQQKPGQSPKALIYSASYRYSGVPD 61 70 80 90 100 110

CDRL3

RFTGSGSGTDFTLTISNVQSEDLAEYFCQQYKTYPFTFGSGTKLEIKRADAAPT

SEQ ID NO: 6: CDR1 sequence of the heavy chain of Ab 1A2
GYTFTSFIMY

SEQ ID NO: 7: CDR2 sequence of the heavy chain of Ab 1A2
DPYNDGTKYNEKFEG

SEQ ID NO: 8: CDR3 sequence of the heavy chain of Ab 1A2
RGNYGNGFAY

SEQ ID NO: 9: CDR1 sequence of the light chain of Ab 1A2
KASQNVGSNVA

SEQ ID NO: 10: CDR2 sequence of the light chain of Ab 1A2
SASHRYS

SEQ ID NO: 11: CDR3 sequence of the light chain of Ab 1A2
QQYYSYPYT

The invention claimed is:

1. A modified influenza haemagglutinin (HA) antigen comprising additional Asn-linked glycosylation on at least two surface patches selected from the group of surface patches consisting of: Site A, Site B, Site C, Site D and Site E;
wherein the coding sequence of the HA has been recombinantly modified to introduce at least two acceptor sites for Asn-linked glycosylation at positions other than at position 11, 23, 154, 165, 286 or 484 of HA of an H5 strain of influenza, or the residues corresponding to these residues in HA from a different strain of influenza;
wherein the acceptor site for Asn-linked glycosylation has the consensus sequence Asn-X-Ser/Thr, wherein X is not Pro.

2. The modified influenza haemagglutinin antigen according to claim 1, comprising additional Asn-linked glycosylation attached to:
i) one or more amino acid residues of Site A, and
ii) one or more amino acid residues of Site B.

3. The modified influenza haemagglutinin antigen of claim 2, further comprising additional Asn-linked glycosylation attached to one or more amino acid residues of Site D.

4. The modified influenza haemagglutinin antigen according to claim 1, comprising additional Asn-linked glycosylation attached to:
i) one or more amino acid residues of Site C,
ii) one or more amino acid residues of Site D, and
iii) one or more amino acid residues of Site E.

5. The modified influenza haemagglutinin antigen of claim 4, further comprising additional Asn-linked glycosylation attached to one or more amino acid residues of Site A.

6. The modified influenza haemagglutinin antigen according to claim 1, comprising additional Asn-linked glycosylation attached to:
i) one or more amino acid residues of Site A,
ii) one or more amino acid residues of Site B, and
iii) one or more amino acid residues of Site E.

7. The modified influenza haemagglutinin antigen of claim 6, further comprising additional Asn-linked glycosylation attached to:
i) one or more amino acid residues of Site C, and
ii) one or more amino acid residues of Site D.

8. The modified influenza haemagglutinin antigen of claim 1, further comprising additional Asn-linked glycosylation attached to one or more amino acid residues of Site A, Site B, Site C, Site D or Site E, or any combination thereof.

9. The modified influenza haemagglutinin antigen of claim 1, wherein the haemagglutinin is from an H1, H2, H3, H5, H7 or H9 strain.

10. The modified influenza haemagglutinin antigen of claim 1, wherein the haemagglutinin is from an H5 strain.

11. The modified influenza haemagglutinin antigen of claim 1, wherein the haemagglutinin lacks the HA stalk, or part of the stalk.

12. A polynucleotide encoding a modified influenza haemagglutinin antigen as described in claim 1.

13. An immunogenic composition comprising a modified influenza haemagglutinin antigen as defined in claim 1 and a pharmaceutically-acceptable carrier.

14. The immunogenic composition according to claim 13, further comprising an adjuvant.

15. The immunogenic composition according to claim 13, wherein the composition is multivalent.

16. A method for producing a modified influenza haemagglutinin antigen comprising expressing a polynucleotide according to claim 12 in a eukaryotic cell.

17. A method of prevention against influenza disease, the method comprising administering an immunogenic composition according to claim 13 to a person in need thereof.

18. The method of claim 17, wherein less than 15 micrograms of haemagglutinin is administered per dose.

19. The method of claim 17, wherein the immunogenic composition prevents influenza caused by a different clade than the clade to which the modified influenza haemagglutinin antigen of the immunogenic composition belongs.

* * * * *